US009925395B2

(12) United States Patent
Gall et al.

(10) Patent No.: US 9,925,395 B2
(45) Date of Patent: Mar. 27, 2018

(54) INNER GANTRY

(71) Applicant: Mevion Medical Systems, Inc., Littleton, MA (US)

(72) Inventors: Kenneth P. Gall, Harvard, MA (US); Stanley J. Rosenthal, Wayland, MA (US); Gordon D. Row, Groton, MA (US); Michael J. Ahearn, Sandown, NH (US)

(73) Assignee: Mevion Medical Systems, Inc., Littleton, MA (US)

( * ) Notice: Subject to any disclaimer, the term of this patent is extended or adjusted under 35 U.S.C. 154(b) by 0 days.

(21) Appl. No.: 15/221,855

(22) Filed: Jul. 28, 2016

(65) Prior Publication Data

US 2017/0028224 A1     Feb. 2, 2017

Related U.S. Application Data

(63) Continuation of application No. 14/542,966, filed on Nov. 17, 2014, now Pat. No. 9,452,301, which is a
(Continued)

(51) Int. Cl.
*A61N 5/10*     (2006.01)
*G21K 5/10*     (2006.01)
(Continued)

(52) U.S. Cl.
CPC ............. *A61N 5/1081* (2013.01); *A61N 5/10* (2013.01); *H05H 7/04* (2013.01); *H05H 13/02* (2013.01);
(Continued)

(58) Field of Classification Search
CPC ...... A61N 5/1081; A61N 5/10; A61N 5/1077; A61N 5/1048; A61N 5/1049;
(Continued)

(56) References Cited

U.S. PATENT DOCUMENTS 2,280,606 A   4/1942   Roberts
2,492,324 A   12/1949  Salisbury
(Continued)

FOREIGN PATENT DOCUMENTS

CA   2629333 A1    5/2007
CN   1537657 A    10/2004
(Continued)

OTHER PUBLICATIONS

18th Japan Conference on Radiation and Radioisotopes [Japanese], Nov. 25-27, 1987, 9 pages.
(Continued)

*Primary Examiner* — David A Vanore
(74) *Attorney, Agent, or Firm* — Choate, Hall & Stewart LLP

(57) ABSTRACT

A system includes a patient support and an outer gantry on which an accelerator is mounted to enable the accelerator to move through a range of positions around a patient on the patient support. The accelerator is configured to produce a proton or ion beam having an energy level sufficient to reach a target in the patient. An inner gantry includes an aperture for directing the proton or ion beam towards the target.

23 Claims, 17 Drawing Sheets

Related U.S. Application Data continuation of application No. 13/532,530, filed on Jun. 25, 2012, now Pat. No. 8,916,843, which is a continuation of application No. 12/275,103, filed on Nov. 20, 2008, now Pat. No. 8,344,340, which is a continuation-in-part of application No. 11/601,056, filed on Nov. 17, 2006, now Pat. No. 7,728,311.

(60) Provisional application No. 60/991,454, filed on Nov. 30, 2007, provisional application No. 60/738,404, filed on Nov. 18, 2005.

(51) Int. Cl.
  *H05H 13/04* (2006.01)
  *H05H 7/04* (2006.01)
  *H05H 13/02* (2006.01)

(52) U.S. Cl.
  CPC ..... *H05H 13/04* (2013.01); *A61N 2005/1087* (2013.01); *H05H 2007/043* (2013.01)

(58) Field of Classification Search
  CPC .. A61N 5/1043; A61N 5/1045; A61N 5/1067; A61N 5/1069; A61N 5/1071; A61N 5/1079; A61N 5/1082; A61N 5/01; A61N 5/103; A61N 5/1042; A61N 5/1047; A61N 5/1065; A61N 5/1083; H05H 13/02; H05H 13/04; H05H 13/005; H05H 7/04; H05H 7/10; H05H 7/12; G21K 1/046; G21K 1/093; G21K 1/04; G21K 1/10; G21K 5/10
  USPC ........ 250/492.3, 396 R, 492.1, 491.1, 505.1, 250/454.11, 492.21, 3, 99, 492.22, 493.1; 315/502, 500, 503, 505, 501, 507; 378/65, 152, 195, 197, 204, 4, 64, 68, 69, 378/9
  See application file for complete search history.

(56) References Cited

U.S. PATENT DOCUMENTS

| | | |
|---|---|---|
| 2,615,129 A | 10/1952 | McMillan |
| 2,659,000 A | 11/1953 | Salisbury |
| 2,958,327 A | 11/1960 | Geismann |
| 3,175,131 A | 3/1965 | Burleigh et al. |
| 3,582,650 A | 6/1971 | Avery |
| 3,679,899 A | 7/1972 | Dimeff |
| 3,689,847 A | 9/1972 | Verster |
| 3,757,118 A | 9/1973 | Hodge et al. |
| 3,867,635 A * | 2/1975 | Brown .................. G21K 1/093 250/396 R |
| 3,868,522 A | 2/1975 | Bigham et al. |
| 3,886,367 A | 5/1975 | Castle, Jr. |
| 3,925,676 A | 12/1975 | Bigham et al. |
| 3,955,089 A | 5/1976 | McIntyre et al. |
| 4,038,622 A | 7/1977 | Purcell |
| 4,047,068 A | 9/1977 | Ress et al. |
| 4,112,306 A | 9/1978 | Nunan |
| 4,139,777 A | 2/1979 | Rautenbach |
| 4,197,510 A | 4/1980 | Szu |
| 4,220,866 A | 9/1980 | Taumann et al. |
| 4,230,129 A | 10/1980 | LeVeen |
| 4,256,966 A | 3/1981 | Heinz |
| 4,336,505 A | 6/1982 | Meyer |
| 4,345,210 A | 8/1982 | Tran |
| 4,353,033 A | 10/1982 | Karasawa |
| 4,425,506 A | 1/1984 | Brown et al. |
| 4,490,616 A | 12/1984 | Cipollina et al. |
| 4,507,614 A | 3/1985 | Prono et al. |
| 4,507,616 A | 3/1985 | Blosser et al. |
| 4,589,126 A | 5/1986 | Augustsson et al. |
| 4,598,208 A | 7/1986 | Brunelli et al. |
| 4,628,523 A | 12/1986 | Heflin |
| 4,633,125 A | 12/1986 | Blosser et al. |
| 4,641,057 A | 2/1987 | Blosser et al. |
| 4,641,104 A | 2/1987 | Blosser et al. |
| 4,651,007 A | 3/1987 | Perusek et al. |
| 4,680,565 A | 7/1987 | Jahnke |
| 4,705,955 A | 11/1987 | Mileikowsky |
| 4,710,722 A | 12/1987 | Jahnke |
| 4,726,046 A | 2/1988 | Nunan |
| 4,734,653 A | 3/1988 | Jahnke |
| 4,737,727 A | 4/1988 | Yamada et al. |
| 4,739,173 A | 4/1988 | Blosser et al. |
| 4,745,367 A | 5/1988 | Dustmann et al. |
| 4,754,147 A | 6/1988 | Maughan et al. |
| 4,769,623 A | 9/1988 | Marsing et al. |
| 4,771,208 A | 9/1988 | Jongen et al. |
| 4,783,634 A | 11/1988 | Yamamoto et al. |
| 4,808,941 A | 2/1989 | Marsing |
| 4,812,658 A | 3/1989 | Koehler |
| 4,843,333 A | 6/1989 | Marsing et al. |
| 4,865,284 A | 9/1989 | Gosis et al. |
| 4,868,843 A | 9/1989 | Nunan |
| 4,868,844 A | 9/1989 | Nunan |
| 4,870,287 A | 9/1989 | Cole et al. |
| 4,880,985 A | 11/1989 | Jones |
| 4,894,541 A | 1/1990 | Ono |
| 4,902,993 A | 2/1990 | Krevet |
| 4,904,949 A | 2/1990 | Wilson |
| 4,905,267 A | 2/1990 | Miller et al. |
| 4,917,344 A * | 4/1990 | Prechter .................. A61N 5/10 248/664 |
| 4,943,781 A | 7/1990 | Wilson et al. |
| 4,987,309 A | 1/1991 | Klasen et al. |
| 4,992,744 A | 2/1991 | Fujita et al. |
| 4,996,496 A | 2/1991 | Kitamura et al. |
| 5,017,789 A | 5/1991 | Young et al. |
| 5,017,882 A | 5/1991 | Finlan |
| 5,036,290 A | 7/1991 | Sonobe et al. |
| 5,039,057 A | 8/1991 | Prechter et al. |
| 5,039,867 A | 8/1991 | Nishihara et al. |
| 5,072,123 A | 12/1991 | Johnsen |
| 5,111,042 A | 5/1992 | Sullivan et al. |
| 5,111,173 A | 5/1992 | Matsuda et al. |
| 5,117,194 A | 5/1992 | Nakanishi et al. |
| 5,117,212 A | 5/1992 | Yamamoto et al. |
| 5,117,829 A | 6/1992 | Miller et al. |
| 5,148,032 A | 9/1992 | Hernandez |
| 5,166,531 A | 11/1992 | Huntzinger |
| 5,189,687 A | 2/1993 | Bova et al. |
| 5,240,218 A | 8/1993 | Dye |
| 5,260,579 A | 11/1993 | Yasuda et al. |
| 5,260,581 A | 11/1993 | Lesyna et al. |
| 5,278,533 A | 1/1994 | Kawaguchi |
| 5,297,037 A | 3/1994 | Ifuku |
| 5,317,164 A | 5/1994 | Kurokawa |
| 5,336,891 A | 8/1994 | Crewe |
| 5,341,104 A | 8/1994 | Anton et al. |
| 5,349,198 A | 9/1994 | Takanaka |
| 5,365,742 A | 11/1994 | Boffito et al. |
| 5,374,913 A | 12/1994 | Pissantezky et al. |
| 5,382,914 A | 1/1995 | Hamm et al. |
| 5,405,235 A | 4/1995 | Lebre et al. |
| 5,440,133 A | 8/1995 | Moyers et al. |
| 5,461,773 A | 10/1995 | Kawaguchi |
| 5,463,291 A * | 10/1995 | Carroll .................. H05H 7/04 29/602.1 |
| 5,511,549 A * | 4/1996 | Legg .................. A61N 5/103 250/252.1 |
| 5,521,469 A | 5/1996 | Laisne |
| 5,561,697 A | 10/1996 | Takafuji et al. |
| 5,585,642 A | 12/1996 | Britton et al. |
| 5,633,747 A | 5/1997 | Nikoonahad |
| 5,668,371 A | 9/1997 | Deasy et al. |
| 5,726,448 A | 3/1998 | Smith et al. |
| 5,751,781 A | 5/1998 | Brown et al. |
| 5,778,047 A | 7/1998 | Mansfield et al. |
| 5,811,944 A | 9/1998 | Sampayan et al. |
| 5,818,058 A * | 10/1998 | Nakanishi .................. A61N 5/10 250/492.3 |

(56) References Cited

U.S. PATENT DOCUMENTS

| | | | |
|---|---|---|---|
| 5,821,705 A | 10/1998 | Caporaso et al. | |
| 5,825,845 A | 10/1998 | Blair et al. | |
| 5,851,182 A | 12/1998 | Sahadevan | |
| 5,866,912 A | 2/1999 | Slater et al. | |
| 5,874,811 A | 2/1999 | Finlan et al. | |
| 5,895,926 A | 4/1999 | Britton et al. | |
| 5,920,601 A | 7/1999 | Nigg et al. | |
| 5,929,458 A | 7/1999 | Nemezawa et al. | |
| 5,993,373 A * | 11/1999 | Nonaka | A61N 5/10 250/492.1 |
| 6,034,377 A | 3/2000 | Pu | |
| 6,057,655 A | 5/2000 | Jongen | |
| 6,061,426 A | 5/2000 | Linders et al. | |
| 6,064,807 A | 5/2000 | Arai et al. | |
| 6,094,760 A | 8/2000 | Nonaka et al. | |
| 6,140,021 A | 10/2000 | Nakasuji et al. | |
| 6,265,837 B1 | 7/2001 | Akiyama et al. | |
| 6,268,610 B1 | 7/2001 | Pu | |
| 6,279,579 B1 | 8/2001 | Riaziat et al. | |
| 6,316,776 B1 | 11/2001 | Hiramoto et al. | |
| 6,380,545 B1 | 4/2002 | Yan | |
| 6,407,505 B1 | 6/2002 | Bertsche | |
| 6,433,336 B1 | 8/2002 | Jongen et al. | |
| 6,433,349 B2 | 8/2002 | Akiyama et al. | |
| 6,441,569 B1 | 8/2002 | Janzow | |
| 6,476,403 B1 | 11/2002 | Dolinskii et al. | |
| 6,501,981 B1 | 12/2002 | Schweikard et al. | |
| 6,519,316 B1 | 2/2003 | Collins | |
| 6,621,889 B1 | 9/2003 | Mostafavi | |
| 6,646,383 B2 | 11/2003 | Bertsche et al. | |
| 6,683,318 B1 | 1/2004 | Haberer et al. | |
| 6,683,426 B1 | 1/2004 | Kleeven | |
| 6,693,283 B2 | 2/2004 | Eickhoff et al. | |
| 6,710,362 B2 | 3/2004 | Kraft et al. | |
| 6,713,773 B1 | 3/2004 | Lyons et al. | |
| 6,717,162 B1 | 4/2004 | Jongen | |
| 6,769,806 B2 | 8/2004 | Moyers | |
| 6,774,383 B2 | 8/2004 | Norimine et al. | |
| 6,777,700 B2 | 8/2004 | Yanagisawa et al. | |
| 6,800,866 B2 | 10/2004 | Amemiya et al. | |
| 6,803,591 B2 | 10/2004 | Muramatsu et al. | |
| 6,814,694 B1 | 11/2004 | Pedroni | |
| 6,853,703 B2 | 2/2005 | Svatos et al. | |
| 6,865,254 B2 * | 3/2005 | Nafstadius | A61N 5/1049 378/4 |
| 6,891,177 B1 | 5/2005 | Kraft et al. | |
| 6,897,451 B2 | 5/2005 | Kaercher et al. | |
| 6,953,943 B2 | 10/2005 | Yanagisawa et al. | |
| 6,965,116 B1 | 11/2005 | Wagner et al. | |
| 6,969,194 B1 * | 11/2005 | Nafstadius | A61N 5/01 378/197 |
| 6,984,835 B2 | 1/2006 | Harada | |
| 6,993,112 B2 | 1/2006 | Hesse | |
| 7,008,105 B2 | 3/2006 | Amann et al. | |
| 7,014,361 B1 | 3/2006 | Ein-Gal | |
| 7,026,636 B2 | 4/2006 | Yanagisawa et al. | |
| 7,041,479 B2 | 5/2006 | Swartz et al. | |
| 7,045,781 B2 | 5/2006 | Adamec et al. | |
| 7,053,389 B2 | 5/2006 | Yanagisawa et al. | |
| 7,091,478 B2 | 8/2006 | Haberer | |
| 7,135,678 B2 | 11/2006 | Wang et al. | |
| 7,138,771 B2 | 11/2006 | Bechthold et al. | |
| 7,154,108 B2 | 12/2006 | Tadokoro et al. | |
| 7,162,005 B2 | 1/2007 | Bjorkholm | |
| 7,173,265 B2 | 2/2007 | Miller et al. | |
| 7,208,748 B2 | 4/2007 | Sliski et al. | |
| 7,247,869 B2 | 7/2007 | Tadokoro et al. | |
| 7,274,018 B2 | 9/2007 | Adamec et al. | |
| 7,295,649 B2 | 11/2007 | Johnsen | |
| 7,297,967 B2 | 11/2007 | Yanagisawa et al. | |
| 7,318,805 B2 | 1/2008 | Schweikard et al. | |
| 7,319,336 B2 | 1/2008 | Baur et al. | |
| 7,348,557 B2 | 3/2008 | Armit | |
| 7,348,579 B2 | 3/2008 | Pedroni | |
| 7,355,189 B2 | 4/2008 | Yanagisawa et al. | |
| 7,453,076 B2 | 11/2008 | Welch et al. | |
| 7,468,506 B2 | 12/2008 | Rogers et al. | |
| 7,473,913 B2 * | 1/2009 | Hermann | A61N 5/10 250/492.3 |
| 7,525,104 B2 | 4/2009 | Harada | |
| 7,541,905 B2 | 6/2009 | Antaya | |
| 7,554,096 B2 | 6/2009 | Ward et al. | |
| 7,554,097 B2 | 6/2009 | Ward et al. | |
| 7,557,358 B2 | 7/2009 | Ward et al. | |
| 7,557,359 B2 | 7/2009 | Ward et al. | |
| 7,557,360 B2 | 7/2009 | Ward et al. | |
| 7,557,361 B2 | 7/2009 | Ward et al. | |
| 7,579,603 B2 | 8/2009 | Birgy et al. | |
| 7,582,866 B2 | 9/2009 | Furuhashi et al. | |
| 7,582,885 B2 | 9/2009 | Katagiri et al. | |
| 7,582,886 B2 * | 9/2009 | Trbojevic | A61N 5/10 250/398 |
| 7,598,497 B2 | 10/2009 | Yamamoto et al. | |
| 7,629,598 B2 | 12/2009 | Harada | |
| 7,656,258 B1 | 2/2010 | Antaya et al. | |
| 7,659,528 B2 | 2/2010 | Uematsu | |
| 7,692,166 B2 | 4/2010 | Muraki et al. | |
| 7,696,847 B2 | 4/2010 | Antaya | |
| 7,728,311 B2 | 6/2010 | Gall | |
| 7,759,642 B2 | 7/2010 | Nir | |
| 7,770,231 B2 | 8/2010 | Prater et al. | |
| 7,786,451 B2 | 8/2010 | Ward et al. | |
| 7,786,452 B2 | 8/2010 | Ward et al. | |
| 7,807,982 B2 | 10/2010 | Nishiuchi et al. | |
| 7,816,657 B2 | 10/2010 | Hansmann et al. | |
| 7,834,334 B2 | 11/2010 | Grozinger et al. | |
| 7,834,336 B2 | 11/2010 | Boeh et al. | |
| 7,848,488 B2 | 12/2010 | Mansfield | |
| 7,857,756 B2 | 12/2010 | Warren et al. | |
| 7,894,574 B1 | 2/2011 | Nord et al. | |
| 7,914,734 B2 | 3/2011 | Livingston | |
| 7,919,765 B2 | 4/2011 | Timmer | |
| 7,943,913 B2 | 5/2011 | Balakin | |
| 7,950,587 B2 | 5/2011 | Henson et al. | |
| 7,977,648 B2 | 7/2011 | Westerly et al. | |
| 7,977,657 B2 | 7/2011 | Flynn et al. | |
| 7,982,198 B2 | 7/2011 | Nishiuchi et al. | |
| 7,986,768 B2 | 7/2011 | Nord et al. | |
| 7,990,524 B2 | 8/2011 | Jureller et al. | |
| 8,009,804 B2 | 8/2011 | Siljamaki et al. | |
| 8,041,006 B2 | 10/2011 | Boyden et al. | |
| 8,053,508 B2 | 11/2011 | Korkut et al. | |
| 8,053,745 B2 | 11/2011 | Moore | |
| 8,053,746 B2 | 11/2011 | Timmer et al. | |
| 8,063,381 B2 | 11/2011 | Tsoupas et al. | |
| 8,067,748 B2 | 11/2011 | Balakin | |
| 8,085,899 B2 | 12/2011 | Nord et al. | |
| 8,089,054 B2 | 1/2012 | Balakin | |
| 8,093,564 B2 | 1/2012 | Balakin | |
| 8,093,568 B2 | 1/2012 | Mackie et al. | |
| 8,129,699 B2 | 3/2012 | Balakin | |
| 8,144,832 B2 | 3/2012 | Balakin | |
| 8,153,989 B2 | 4/2012 | Tachikawa et al. | |
| 8,173,981 B2 | 5/2012 | Trbojevic | |
| 8,188,688 B2 | 5/2012 | Balakin | |
| 8,198,607 B2 | 6/2012 | Balakin | |
| 8,227,768 B2 | 7/2012 | Smick et al. | |
| 8,232,536 B2 | 7/2012 | Harada | |
| 8,288,742 B2 | 10/2012 | Balakin | |
| 8,294,127 B2 | 10/2012 | Tachibana | |
| 8,304,725 B2 | 11/2012 | Komuro et al. | |
| 8,304,750 B2 | 11/2012 | Preikszas et al. | |
| 8,309,941 B2 | 11/2012 | Balakin | |
| 8,330,132 B2 | 12/2012 | Guertin et al. | |
| 8,334,520 B2 | 12/2012 | Otaka et al. | |
| 8,335,397 B2 | 12/2012 | Takane et al. | |
| 8,344,340 B2 | 1/2013 | Gall et al. | |
| 8,350,214 B2 | 1/2013 | Otaki et al. | |
| 8,368,038 B2 | 2/2013 | Balakin | |
| 8,373,143 B2 | 2/2013 | Balakin | |
| 8,373,145 B2 | 2/2013 | Balakin | |
| 8,378,299 B2 | 2/2013 | Frosien | |
| 8,378,321 B2 | 2/2013 | Balakin | |
| 8,382,943 B2 | 2/2013 | Clark | |

(56) References Cited

U.S. PATENT DOCUMENTS

| | | | |
|---|---|---|---|
| 8,399,866 B2 | 3/2013 | Balakin | |
| 8,405,042 B2 | 3/2013 | Honda et al. | |
| 8,405,056 B2 | 3/2013 | Amaldi et al. | |
| 8,415,643 B2 | 4/2013 | Balakin | |
| 8,416,918 B2 | 4/2013 | Nord et al. | |
| 8,421,041 B2 | 4/2013 | Balakin | |
| 8,426,833 B2 | 4/2013 | Trbojevic | |
| 8,436,323 B2 | 5/2013 | Iseki et al. | |
| 8,440,987 B2 | 5/2013 | Stephani et al. | |
| 8,445,872 B2 | 5/2013 | Behrens et al. | |
| 8,466,441 B2 | 6/2013 | Iwata et al. | |
| 8,472,583 B2 | 6/2013 | Star-Lack et al. | |
| 8,483,357 B2 | 7/2013 | Siljamaki et al. | |
| 8,487,278 B2 | 7/2013 | Balakin | |
| 8,552,406 B2 | 10/2013 | Phaneuf et al. | |
| 8,552,408 B2 | 10/2013 | Hanawa et al. | |
| 8,569,717 B2 | 10/2013 | Balakin | |
| 8,581,215 B2 | 11/2013 | Balakin | |
| 8,581,523 B2 | 11/2013 | Gall et al. | |
| 8,581,525 B2 | 11/2013 | Antaya et al. | |
| 8,653,314 B2 | 2/2014 | Pelati et al. | |
| 8,653,473 B2 | 2/2014 | Yajima | |
| 8,766,218 B2 | 7/2014 | Jongen | |
| 8,779,393 B2 * | 7/2014 | Sasai | A61N 5/1081 250/396 R |
| 8,791,656 B1 * | 7/2014 | Zwart | H05H 7/04 315/500 |
| 8,907,311 B2 | 12/2014 | Gall et al. | |
| 8,916,843 B2 | 12/2014 | Gall et al. | |
| 8,927,950 B2 * | 1/2015 | Gall | A61N 5/1077 250/492.1 |
| 9,155,186 B2 * | 10/2015 | Zwart | H05H 7/04 |
| 9,185,789 B2 * | 11/2015 | Zwart | H05H 13/02 |
| 9,301,384 B2 * | 3/2016 | Zwart | H05H 7/04 |
| 9,333,375 B2 * | 5/2016 | Arber | A61N 5/1067 |
| 9,452,301 B2 | 9/2016 | Gall et al. | |
| 9,545,528 B2 * | 1/2017 | Gall | H05H 13/02 |
| 9,622,335 B2 * | 4/2017 | Gall | H05H 13/02 |
| 2003/0048080 A1 | 3/2003 | Amemiya et al. | |
| 2003/0125622 A1 | 7/2003 | Schweikard et al. | |
| 2003/0152197 A1 * | 8/2003 | Moyers | A61B 6/0407 378/204 |
| 2003/0163015 A1 * | 8/2003 | Yanagisawa | A61N 5/10 600/1 |
| 2003/0183779 A1 | 10/2003 | Norimine et al. | |
| 2004/0000650 A1 | 1/2004 | Yanagisawa et al. | |
| 2004/0056212 A1 | 3/2004 | Yanagisawa et al. | |
| 2004/0061077 A1 | 4/2004 | Muramatsu et al. | |
| 2004/0061078 A1 | 4/2004 | Muramatsu et al. | |
| 2004/0098445 A1 | 5/2004 | Baumann et al. | |
| 2004/0111134 A1 | 6/2004 | Muramatsu et al. | |
| 2004/0118081 A1 | 6/2004 | Reimoser et al. | |
| 2004/0149934 A1 | 8/2004 | Yanagisawa et al. | |
| 2004/0159795 A1 | 8/2004 | Kaercher et al. | |
| 2004/0173763 A1 | 9/2004 | Moriyama et al. | |
| 2004/0174958 A1 | 9/2004 | Moriyama et al. | |
| 2004/0183033 A1 | 9/2004 | Moriyama et al. | |
| 2004/0183035 A1 | 9/2004 | Yanagisawa et al. | |
| 2004/0200982 A1 | 10/2004 | Moriyama et al. | |
| 2004/0200983 A1 | 10/2004 | Fujimaki et al. | |
| 2004/0213381 A1 * | 10/2004 | Harada | G21K 1/046 378/152 |
| 2004/0227104 A1 | 11/2004 | Matsuda et al. | |
| 2004/0232356 A1 | 11/2004 | Norimine et al. | |
| 2004/0240626 A1 | 12/2004 | Moyers | |
| 2005/0058245 A1 | 3/2005 | Ein-Gal | |
| 2005/0089141 A1 | 4/2005 | Brown | |
| 2005/0161618 A1 * | 7/2005 | Pedroni | A61N 5/10 250/492.3 |
| 2005/0228255 A1 | 10/2005 | Saracen et al. | |
| 2005/0234327 A1 | 10/2005 | Saracen et al. | |
| 2005/0247890 A1 | 11/2005 | Norimine et al. | |
| 2006/0067468 A1 | 3/2006 | Rietzel | |
| 2006/0173294 A1 | 8/2006 | Ein-Gal | |
| 2007/0001128 A1 | 1/2007 | Sliski et al. | |
| 2007/0023699 A1 | 2/2007 | Yamashita et al. | |
| 2007/0029510 A1 | 2/2007 | Hermann et al. | |
| 2007/0051904 A1 | 3/2007 | Kaiser et al. | |
| 2007/0114945 A1 | 5/2007 | Mattaboni et al. | |
| 2007/0133752 A1 | 6/2007 | Ein-Gal | |
| 2007/0170994 A1 | 7/2007 | Peggs et al. | |
| 2007/0171015 A1 | 7/2007 | Antaya | |
| 2007/0181519 A1 | 8/2007 | Khoshnevis | |
| 2007/0284548 A1 | 12/2007 | Kaiser et al. | |
| 2009/0101832 A1 | 4/2009 | Diehl | |
| 2009/0200483 A1 * | 8/2009 | Gall | A61N 5/1081 250/396 R |
| 2010/0038552 A1 | 2/2010 | Trbojevic | |
| 2010/0192303 A1 | 8/2010 | Miller et al. | |
| 2010/0230617 A1 | 9/2010 | Gall | |
| 2011/0220809 A1 | 9/2011 | Yajima et al. | |
| 2012/0126140 A1 | 5/2012 | Gall et al. | |
| 2012/0313003 A1 | 12/2012 | Trbojevic | |
| 2013/0237425 A1 | 9/2013 | Leigh et al. | |
| 2014/0091734 A1 * | 4/2014 | Gall | A61N 5/1065 315/502 |
| 2014/0094643 A1 | 4/2014 | Gall et al. | |
| 2014/0097920 A1 | 4/2014 | Goldie et al. | |
| 2015/0174429 A1 * | 6/2015 | Zwart | A61N 5/1043 250/396 R |
| 2015/0231411 A1 * | 8/2015 | O'Neal, III | A61N 5/1043 600/1 |

FOREIGN PATENT DOCUMENTS

| | | |
|---|---|---|
| CN | 101061759 A | 10/2007 |
| CN | 101361156 | 2/2009 |
| CN | 101932361 A | 12/2010 |
| CN | 101933405 A | 12/2010 |
| CN | 101933406 A | 12/2010 |
| CN | 103252024 A | 8/2013 |
| CN | ZL200780102281.X | 9/2013 |
| DE | 2753397 A1 | 6/1978 |
| DE | 3148100 A1 | 6/1983 |
| DE | 3530446 A1 | 3/1986 |
| DE | 4101094 C1 | 5/1992 |
| DE | 4411171 A1 | 10/1995 |
| EP | 0194728 A1 | 9/1986 |
| EP | 0208163 A1 | 1/1987 |
| EP | 0221987 A1 | 5/1987 |
| EP | 0222786 A1 | 5/1987 |
| EP | 0277521 A2 | 8/1988 |
| EP | 0306966 A2 | 3/1989 |
| EP | 0388123 A2 | 9/1990 |
| EP | 0465597 A1 | 1/1992 |
| EP | 0499253 A2 | 8/1992 |
| EP | 0776595 A1 | 6/1997 |
| EP | 0864337 A2 | 9/1998 |
| EP | 0911064 A2 | 4/1999 |
| EP | 1069809 A1 | 1/2001 |
| EP | 1153398 A1 | 11/2001 |
| EP | 1294445 A2 | 3/2003 |
| EP | 1348465 A1 | 10/2003 |
| EP | 1358908 A1 | 11/2003 |
| EP | 1371390 A1 | 12/2003 |
| EP | 1402923 A1 | 3/2004 |
| EP | 1419801 A1 | 5/2004 |
| EP | 1430932 A1 | 6/2004 |
| EP | 1454653 A1 | 9/2004 |
| EP | 1454654 A2 | 9/2004 |
| EP | 1454655 A2 | 9/2004 |
| EP | 1454656 A2 | 9/2004 |
| EP | 1454657 A2 | 9/2004 |
| EP | 1477206 A1 | 11/2004 |
| EP | 1605742 A1 | 12/2005 |
| EP | 1738798 A2 | 1/2007 |
| EP | 1826778 A2 | 8/2007 |
| EP | 1949404 A2 | 7/2008 |
| EP | 2183753 A1 | 5/2010 |
| EP | 2227295 A1 | 9/2010 |
| EP | 2232961 A1 | 9/2010 |
| EP | 2232962 A2 | 9/2010 |

(56) References Cited

FOREIGN PATENT DOCUMENTS

| | | |
|---|---|---|
| EP | 2363170 A1 | 9/2011 |
| EP | 2363171 A1 | 9/2011 |
| EP | 2389977 A2 | 11/2011 |
| EP | 2389978 A2 | 11/2011 |
| EP | 2389979 A2 | 11/2011 |
| EP | 2389980 A2 | 11/2011 |
| EP | 2389981 A2 | 11/2011 |
| EP | 2389982 A2 | 11/2011 |
| EP | 2389983 A2 | 11/2011 |
| EP | 2394498 A2 | 12/2011 |
| EP | 2581110 A1 | 4/2013 |
| EP | 2591821 A1 | 5/2013 |
| FR | 2560421 A1 | 8/1985 |
| FR | 2911843 A1 | 8/2008 |
| GB | 0957342 A | 5/1964 |
| GB | 2015821 A | 9/1979 |
| GB | 2361523 A | 10/2001 |
| HK | 1184404 A1 | 11/2015 |
| JP | S47-028762 U | 12/1972 |
| JP | S48-108098 | 12/1973 |
| JP | 57-162527 | 10/1982 |
| JP | S58-141000 | 8/1983 |
| JP | S61-225798 | 10/1986 |
| JP | 62-150804 | 7/1987 |
| JP | 62-186500 | 8/1987 |
| JP | 63-149344 | 6/1988 |
| JP | 63-218200 | 9/1988 |
| JP | 63-226899 | 9/1988 |
| JP | 64-89621 | 4/1989 |
| JP | 01-276797 | 11/1989 |
| JP | 01-302700 | 12/1989 |
| JP | 4-94198 | 3/1992 |
| JP | 04-129768 B2 | 4/1992 |
| JP | 05-341352 B2 | 12/1993 |
| JP | 06-036893 | 2/1994 |
| JP | 06-233831 | 8/1994 |
| JP | H07-503669 A | 4/1995 |
| JP | 07-260939 | 10/1995 |
| JP | 07-263196 | 10/1995 |
| JP | H07-255867 A | 10/1995 |
| JP | 08-173890 | 7/1996 |
| JP | 08-264298 | 10/1996 |
| JP | 09-162585 | 6/1997 |
| JP | 10-071213 | 3/1998 |
| JP | 11-47287 | 2/1999 |
| JP | 11-102800 | 4/1999 |
| JP | 11-243295 | 9/1999 |
| JP | 2000-294399 A | 10/2000 |
| JP | 2001-006900 A | 1/2001 |
| JP | 2001-009050 A | 1/2001 |
| JP | 2001-129103 A | 5/2001 |
| JP | 2001-137372 A | 5/2001 |
| JP | 2001-346893 A | 12/2001 |
| JP | 2002-164686 A | 6/2002 |
| JP | 2002-263090 A | 9/2002 |
| JP | 2003-503120 A | 1/2003 |
| JP | 2003-517755 A | 5/2003 |
| JP | 2003-215299 A | 7/2003 |
| JP | 2005-526578 A | 9/2005 |
| JP | 2005-538785 A | 12/2005 |
| JP | 2008-507826 A | 3/2008 |
| JP | 04-128717 B2 | 7/2008 |
| JP | 2009-515671 A | 4/2009 |
| JP | 2009-516905 A | 4/2009 |
| JP | 04-273409 B2 | 6/2009 |
| JP | 2009-192244 A | 8/2009 |
| JP | 04-337300 B2 | 9/2009 |
| JP | 43-23267 B2 | 9/2009 |
| JP | 2010-536131 A | 11/2010 |
| JP | 2011-505191 A | 2/2011 |
| JP | 2011-505670 A | 2/2011 |
| JP | 2011-507151 A | 3/2011 |
| JP | 05-046928 B2 | 10/2012 |
| JP | 2013-106980 A | 6/2013 |
| JP | 2013-106981 A | 6/2013 |
| JP | 5221669 B2 | 6/2013 |
| JP | 5368103 B2 | 12/2013 |
| JP | 5662502 B2 | 1/2015 |
| JP | 5662503 B2 | 1/2015 |
| JP | 5695122 B2 | 4/2015 |
| JP | 61-80800 | 8/2017 |
| SU | 300137 | 11/1969 |
| SU | 569635 A1 | 8/1977 |
| TW | 200930160 A | 7/2009 |
| TW | 200934682 A | 8/2009 |
| TW | 200939908 A | 9/2009 |
| TW | 200940120 A | 10/2009 |
| TW | I448313 B | 8/2014 |
| WO | WO-1986/07229 A1 | 12/1986 |
| WO | WO-1990/012413 A1 | 10/1990 |
| WO | WO-1992/03028 A1 | 2/1992 |
| WO | WO-1993/02536 A1 | 2/1993 |
| WO | WO-1993/015882 A1 | 8/1993 |
| WO | WO-1998/17342 A2 | 4/1998 |
| WO | WO-1999/39385 A1 | 8/1999 |
| WO | WO-2000/40064 | 7/2000 |
| WO | WO-2000/49624 | 8/2000 |
| WO | WO-2001/026230 | 4/2001 |
| WO | WO-2001/026569 A1 | 4/2001 |
| WO | WO-02/07817 | 1/2002 |
| WO | WO-2003/018132 | 3/2003 |
| WO | WO-2003/039212 | 5/2003 |
| WO | WO-2003/092812 A1 | 11/2003 |
| WO | WO-2004/026401 A1 | 4/2004 |
| WO | WO-2004/101070 A1 | 11/2004 |
| WO | WO-2006/012467 A2 | 2/2006 |
| WO | WO-2007/061937 A2 | 5/2007 |
| WO | WO-2007/084701 A1 | 7/2007 |
| WO | WO-2007/130164 A2 | 11/2007 |
| WO | WO-2007/145906 A2 | 12/2007 |
| WO | WO-2008/030911 A2 | 3/2008 |
| WO | WO-2008/081480 A1 | 7/2008 |
| WO | WO-2009/048745 A2 | 4/2009 |
| WO | WO-2009/070173 A1 | 6/2009 |
| WO | WO-2009/070588 A1 | 6/2009 |
| WO | WO-2009/073480 A2 | 6/2009 |

OTHER PUBLICATIONS

510(k) Summary: Ion Beam Applications S.A., FDA, Jul. 12, 2001, 5 pages.

510(k) Summary: Optivus Proton Beam Therapy System, Jul. 21, 2000, 5 pages.

Abrosimov et al., "1000MeV Proton Beam Therapy facility at Petersburg Nuclear Physics Institute Synchrocyclotron," Medical Radiology (Moscow) 32, 10 (1987) revised in Journal of Physics, Conference Series 41, 2006, pp. 424-432, Institute of Physics Publishing Limited.

Adachi et al., "A 150MeV FFAG Synchrotron with "Return-Yoke Free" Magent," Proceedings of the 2001 Particle Accelerator Conference, Chicago, 2001, 3 pages.

Ageyev et al., "The IHEP Accelerating and Storage Complex (UNK) Status Report," 11th International Conference on High-Energy Accelerators, 1980, pp. 60-70.

Agosteo et al., "Maze Design of a gantry room for proton therapy," Nuclear Instruments & Methods In Physics Research, 1996, Section A, 382, pp. 573-582.

Alexeev et al., "R4 Design of Superconducting Magents for Proton Synchrotrons," Proceedings of the Fifth International Cryogenic Engineering Conference, 197 4, pp. 531-533.

Allardyce et al., "Performance and Prospects of the Reconstructed CERN 600 MeV Synchrocyclotron," IEEE Transactions on Nuclear Science USA, Jun. 1977, ns-24:(3) 1631-1633.

Alonso, "Magnetically Scanned Ion Beams for Radiation Therapy," Accelerator & Fusion Research Division, Lawrence Berkeley Laboratory, Berkeley, CA, Oct. 1988, 13 pages.

Amaldi et al., "The Italian project for a hadrontherapy centre" Nuclear Instruments and Methods in Physics Research A, 1995, 360, pp. 297-301.

Amaldi, "Overview of the world landscape of Hadrontherapy and the projects of the TERA foundation," Physica Medica, An Inter-

(56) References Cited

OTHER PUBLICATIONS national journal Devoted to the Applications of Physics to Medicine and Biology, Jul. 1998, vol. XIV, Supplement 1, 6th Workshop on Heavy Charged Particles in Biology and Medicine, Instituto Scientific Europeo (ISE), Sep. 29-Oct. 1, 1977, Baveno, pp. 76-85.
An Accelerated Collaboration Meets with Beaming Success, Lawrence Livermore National Laboratory, Apr. 12, 2006, S&TR, Livermore, California, pp. 1-3, http://www.llnl.gov/str/April06/Caporaso.html.
Anferov et al., "Status of the Midwest Proton Radiotherapy Institute," Proceedings of the 2003 Particle Accelerator Conference,2003, pp. 699-701.
Anferov et al., "The Indiana University Midwest Proton Radiation Institute," Proceedings of the 2001 Particle Accelerator Conference, 2001, Chicago, pp. 645-647.
Appun, "Various 12roblems of magnet fabrication for high-energy accelerators," Journal for All Engineers Interested in the Nuclear Field, 1967, 12 pp. 10-16 (1967) [Lang.: German], English bibliographic information (htto://www.osti.gov/energvcitations/oroduct.biblio.iso?ostiid=4442292).
Arduini et al. "Physical specifications of clinical proton beams from a synchrotron," Med. Phys, Jun. 1996, 23 ( 6): 939-951.
Badano et al., "Proton-Ion Medical Machine Study (PIMMS) Part I," PIMMS, Jan. 1999, 238 pages.
Beam Delivery and Properties, Journal of the ICRU, 2007, 7(2):20 pages.
Beeckman et al., "Preliminary design of a reduced cost proton therapy facility using a compact, high field isochronous cyclotron," Nuclear Instruments and Methods in Physics Reasearch B56/57, 1991, pp. 1201-1204.
Bellomo et al., "The Superconducting Cyclotron Program at Michigan State University," Bulletin of the American Physical Society, Sep. 1980, 25(7):767.
Benedikt and Carli, "Matching to Gantries for Medical Synchrotrons" IEEE Proceedings of the 1997 Particle Accelerator Conference, 1997, pp. 1379-1381.
Bieth et al., "A Very Compact Protontherapy Facility Based on an Extensive Use of High Temperature Superconductors (HTS)" Cyclotrons and their Applications 1998, Proceedings of the Fifteenth International Conference on Cyclotrons and their Applications, Caen, Jun. 14-19, 1998, pp. 669-672.
Bigham, "Magnetic Trim Rods for Superconducting Cyclotrons," Nuclear Instruments and Methods (North-Holland Publishing Co.), 1975, 141:223-228.
Bimbot, "First Studies of the External Beam from the Orsay S.C. 200 MeV," Institut de Physique Nucleaire, BP 1, Orsay, France, IEEE, 1979, pp. 1923-1926.
Blackmore et al., "Operation of the Triumf Proton Therapy Facility," IEEE Proceedings of the 1997 Particle Accelerator Conference, May 12-16, 19973:3831-3833.
Bloch, "The Midwest Proton Therapy Center," Application of Accelerators in Research and Industry, Proceedings of the Fourteenth Int'l. Conf, Part Two, Nov. 1996, pp. 1253-1255.
Blosser et al., "A Compact Superconducting Cyclotron for the Production of High Intensity Protons," Proceedings of the 1997 Particle Accelerator Conference, May 12-16, 1997, 1:1054-1056.
Blosser et al., "Advances in Superconducting Cyclotrons at Michigan State University," Proceedings of the 11th International Conference on Cyclotrons and their Applications, Oct. 1986, pp. 157-167, Tokyo.
Blosser et al., "Characteristics of a 400 (Q2/A) MeV Super-Conducting Heavy-Ion Cyclotron," Bulletin of the American Physical Society, Oct. 1974, p. 1026.
Blosser et al., "Medical Accelerator Projects at Michigan State Univ." IEEE Proceedings of the 1989 Particle Accelerator Conference, Mar. 20-23, 1989, 2:742-746.
Blosser et al., "Problems and Accomplishments of Superconducting Cyclotrons," Proceedings of the 14th International Conference, Cyclotrons and Their Applications, Oct. 1995, pp. 674-684.
Blosser et al., "Progress toward an experiment to study the effect of RF grounding in an internal ion source on axial oscillations of the beam in a cyclotron," National Superconducting Cyclotron Laboratory, Michigan State University, Report MSUCL-760, CP600, Cyclotrons and their Applications 2011, Sixteenth International Conference, 2001, pp. 274-276.
Blosser et al., "Superconducting Cyclotron for Medical Application", IEEE Transactions on Magnetics, Mar. 1989, 25(2): 1746-1754.
Blosser et al., "Superconducting Cyclotrons", Seventh International Conference on Cyclotrons and their Applications, Aug. 19-22, 1975, pp. 584-594.
Blosser, "Application of Superconductivity in Cyclotron Construction," Ninth International Conference on Cyclotrons and their Applications, Sep. 1981, pp. 147-157.
Blosser, "Applications of Superconducting Cyclotrons," Twelfth International Conference on Cyclotrons and Their Applications, May 8-12, 1989, pp. 137-144.
Blosser, "Future Cyclotrons," AIP, The Sixth International Cyclotron Conference, 1972, pp. 16.
Blosser, "Medical Cyclotrons," Physics Today, Special Issue Physical Review Centenary, Oct. 1993, pp. 70-73.
Blosser, "Preliminary Design Study Exploring Building Features Required for a Proton Therapy Facility for the Ontario Cancer Institute", Mar. 1991, MSUCL-760a, 53 pages.
Blosser, "Progress on the Coupled Superconducting Cyclotron Project," Bulletin of the American Physical Society, Apr. 1981, 26(4):558.
Blosser, "Synchrocyclotron Improvement Programs," IEEE Transactions on Nuclear Science USA, Jun. 1969, 16(3):Part I, pp. 405-414.
Blosser, "The Michigan State University Superconducting Cyclotron Program," Nuclear Science, Apr. 1979, NS-26(2):2040-2047.
Blosser, H., Present and Future Superconducting Cyclotrons, Bulletin of the American Physical Society, Feb. 1987, 32(2):171 Particle Accelerator Conference, Washington, D.C.
Blosser, H.G., "Superconducting Cyclotrons at Michigan State University", Nuclear Instruments & Methods in Physics Research, 1987,vol. B 24/25, part II, pp. 752-756.
Botha et al., "A New Multidisciplinary Separated-Sector Cyclotron Facility," IEEE Transactions on Nuclear Science, 1977, NS-24(3): 1118-1120.
Canadian Office action from corresponding Canadian Application No. 2707012 dated May 1, 2014 (6 pages).
Cancer Clinics, 1997, 43(2):209-214 [Lang.: Japanese].
Chichili et al., "Fabrication ofNb3Sn Shell-Type Coils with Pre-Preg Ceramic Insulation," American Institute of Physics Conference Proceedings, AIP USA, No. 711, (XP-002436709, ISSN: 0094-243X), 2004, pp. 450-457.
Chinese office action with English translation from Chinese application 200780102281.X dated Dec. 7, 2011 (15 pages).
Chinese office action with English translation from Chinese application 200780102281.X dated Oct. 23, 2012 (14 pages).
Chong et al., Radiology Clinic North American 7, 3319, 1969, 27 pages.
Chu et al., "Instrumentation for Treatment of Cancer Using Proton and Light-ion Beams," Review of Scientific Instruments, Aug. 1993, 64 (8):2055-2122.
Chu et al., "Performance Specifications for Proton Medical Facility," Lawrence Berkeley Laboratory, University of California, Mar. 1993, 128 pages.
Chu, "Instrumentation in Medical Systems," Accelerator and Fusion Research Division, Lawrence Berkeley Laboratory, University of California, Berkeley, CA, May 1995, 9 pages.
Cole et al., "Design and Application of a Proton Therapy Accelerator," Fermi National Accelerator Laboratory, IEEE, 1985, 5 pages.
Collins, et al., "The Indiana University Proton Therapy System," Proceedings of EPAC 2006, Edinburgh, Scotland, 2006, 3 pages.
Comadi et al., "Proposed New Facilities for Proton Therapy at iThemba Labs," Proceedings of EPAC, 2002, pp. 560-562.
Communication pursuant to Article 94(3) EPC for 11177602.7, 5 pages (dated May 12, 2016).

(56) References Cited

OTHER PUBLICATIONS

Communication pursuant to Article 94(3) EPC for EP11177602.7, 4 pages (dated Mar. 17, 2017).
C/E Source of Ions for Use in Sychro-Cyclotrons Search, dated Jan. 31, 2005, 9 pages.
Source Search "Cites of U.S. and Foreign Patents/Published applications in the name of Mitsubishi Denki Kabushiki Kaisha and Containing the Keywords (Proton and Synchrocyclotron)," dated Jan. 2005, 8 pages.
Cosgrove et al., "Microdosimetric Studies on the Orsay Proton Synchrocyclotron at 73 and 200 MeV," Radiation Protection Dosimetry, 1997, 70(1-4):493-496.
Coupland, "High-field (5 T) pulsed superconducting dipole magnet," Proceedings of the Institution of Electrical Engineers, Jul. 1974, 121(7):771-778.
Coutrakon et al. "Proton Synchrotrons for Cancer Therapy," Application of Accelerators in Research and Industry- Sixteenth International Conf., American Institute of Physics, Nov. 1-5, 2000, vol. 576, pp. 861-864.
Coutrakon et al., "A prototype beam delivery system for the proton medical accelerator at Loma Linda," Medical Physics, Nov./Dec. 1991, 18(6)1093-1099.
CPAC Highlights Its Proton Therapy Program at ESTRO Annual Meeting, TomoTherapy Incorporated, Sep. 18, 2008, Madison, Wisconsin, pp. 1-2.
Cuttone, "Applications of a Particle Accelerators in Medical Physics," Istituto Nazionale di Fisica Nucleare-Laboratori Nazionali del Sud, V.S. Sofia, 44 Cantania, Italy, Jan. 2010, 17 pages.
Dahl P, "Superconducting Magnet System," American Institute of Physics, AIP Conference Proceedings, 1987-1988, 2: 1329-1376.
Dialog Search, dated Jan. 31, 2005, 17 pages.
Dugan et al., "Tevatron Status" IEEE, Particle Accelerator Conference, Accelerator Science & Technology, 1989, pp. 426-430.
Eickhoff et al., "The Proposed Accelerator Facility for Light Ion Cancer Therapy in Heidelberg," Proceedings of the 1999 Particle Accelerator Conference, New York, 1999, pp. 2513-2515.
Enchevich et al., "Minimizing Phase Losses in the 680 MeV Synchrocyclotron by Correcting the Accelerating Voltage Amplitude," Atomnava EnerRiva, 1969, 26:(3):315-316.
Endo et al., "Compact Proton and Carbon Ion Synchrotrons for Radiation Therapy," Proceedings of EPAC 2002, Paris France, 2002, pp. 2733-2735.
English Translation of Notification of Reasons for Rejection in Japanese Application No. 2010-536130 dated Jun. 4, 2013.
European Communication from European application 06838033.6 dated Jun. 27, 2013 (5 pages).
European office action from European application 07868958.5 dated Jul. 16, 2010 (2 pages).
European office action from European application 11165422.4 dated Apr. 17, 2012 (7 pages).
European office action from European application 11165423.2 dated Apr. 17, 2012 (5 pages).
European office action from European application 11165423.2 dated Sep. 2, 2011 (5 pages).
European office action from European application 12193833.6 dated Mar. 27, 2013 (7 pages).
European office action from European application 12193850.0 dated Feb. 24, 2015 (51 pages).
European office action from European application 12193850.0 dated Jul. 2, 2013 (9 pages).
European office action from European application 12193850.0 dated Mar. 18, 2015 (52 pages).
Examination Report from European Application No. 11177601.9 dated Jun. 27, 2013 (6 pages).
File history of European application 11177602.7 dated Dec. 6, 2013 (148 pages).
File history of European application 11177603.5 dated Oct. 30, 2013 (149 pages).
File history of European application 11177605.0 dated Oct. 30, 2013 (148 pages).
File history of European application 11177606.8 dated Oct. 30, 2013 (152 pages).
File history of European application 11177607.6 dated Oct. 30, 2013 (135 pages).
File history of European application No. 11177601.9 dated Oct. 30, 2013 (157 pages).
File History of U.S. Pat. No. 8,581,523 (downloaded Nov. 14, 2013).
Flanz et al., "Large Medical Gantries," Particle Accelerator Conference, Massachusetts General Hospital, 1995, pp. 1-5.
Flanz et al., "Operation of a Cyclotron Based Proton Therapy Facility", Massachusetts General Hospital, Boston, MA 02114, pp. 1-4, retrieved from Internet in 2009.
Flanz et al., "The Northeast Proton Therapy Center at Massachusetts General Hospital," Fifth Workshop on Heavy Charge Particles in Biology and Medicine, GSI, Darmstadt, Aug. 1995, 11 pages.
Flanz et al., "Treating Patients with the NPTC Accelerator Based Proton Treatment Facility," Proceedings of the 2003 Particle Accelerator Conference, 2003, pp. 690-693.
Flood and Frazier, "The Wide-Band Driven RF System for the Berkeley 88-Inch Cyclotron," American Institute of Physics, Conference Proceedings., No. 9, 1972, 459-466.
Foster and Kashikhin, "Superconducting Superferric Dipole Magent with Cold Iron Core for the VLHC," IEEE Transactions on Applied Superconductivity, Mar. 2002, 12(1):111-115.
Friesel et al., "Design and Construction Progress on the IUCF Midwest Proton Radiation Institute," Proceedings of EPAC 2002, 2002, pp. 2736-2738.
Fukumoto et al., "A Proton Therapy Facility Plan" Cyclotrons and their Applications, Proceedings of the 13th International Conference, Vancouver, Canada, Jul. 6-10, 1992, pp. 258-261.
Fukumoto, "Cyclotron Versus Synchrotron for Proton Beam Therapy," KEK Prepr., No. 95-122, Oct. 1995, pp. 533-536.
Goto et al., "Progress on the Sector Magnets for the Riken SRC," American Institute of Physics, CP600, Cyclotrons and Their Applications 2001, Sixteenth International Conference, 2001, pp. 319-323.
Graffman et al., "Design Studies for a 200 MeV Proton Clinic for Radiotherapy," AIP Conference Proceedings: Cyclotrons—1972, 1972, No. 9, pp. 603-615.
Graffman, et. al. "Proton radiotherapy with the Uppsala cyclotron. Experience and plans" Strahlentherapie, 1985, 161(12):764-770.
Graffman, S., et al., Clinical Trials in Radiotherapy and the Merits of High Energy Protons, Acta Radiol. Therapy Phys. Biol. 9:1-23 (1970).
Hede, "Research Groups Promoting Proton Therapy "Lite,"" Journal of the National Cancer Institute, Dec. 6, 2006, 98(23):1682-1684.
Heinz, "Superconducting Pulsed Magnetic Systems for High-Energy Synchrotrons," Proceedings of the Fourth International Cryogenic Engineering Conference, May 24-26, 1972, pp. 55-63.
Hentschel et al., "Plans for the German National Neutron Therapy Centre with a Hospital-Based 70 MeV Proton Cyclotron at University Hospital Essen/Germany," Cyclotrons and their Applications, Proceedings of the Fifteenth International Conference on Cyclotrons and their Applications, Caen, Franco, Jun. 14-19, 1998, pp. 21-23.
Hepburn et al., "Superconducting Cyclotron Neutron Source for Therapy," International Journal of Radiation Oncology Biology Physics, vol. 3 complete, 1977, pp. 387-391.
Hirabayashi, "Development of Superconducting Magnets for Beam Lines and Accelerator at KEK," IEEE Transaction on Magnetics, Jan. 1981, Mag-17(1 ):728-731.
Indiana's mega-million proton therapy cancer center welcomes its first patients [online] Press 719 release, Health & Medicine Week, 2004, retrieved from NewsRx.com, Mar. 1, 2004, pp. 119-120.
Ishibashi and Mcinturff, "Stress Analysis of Superconducting 1 OT Magnets for Synchrotron," Proceedings of the Ninth International Cryogenic Engineering Conference, May 11-14, 1982, pp. 513-516.
Ishibashi and Mcinturff, "Winding Design Study of Superconducting 10 T Dipoles for a Synchrotron," IEEE Transactions on Magnetics, May 1983, MAG-19(3):1364-1367.

(56) References Cited

OTHER PUBLICATIONS

Jahnke et al., "First Superconducting Prototype Magnets for a Compact Synchrotron Radiation Source in Operation," IEEE Transactions on Magnetics, Mar. 1988, 24(2):1230-1232.
Japanese Office Action from corresponding Japanese application No. 2013-098461 dated May 12, 2014 (15 pages).
Japanese office action with English translation from Japanese application 2010-535942 dated Jun. 19, 2012 (6 pages).
Japanese office action with English translation from Japanese application 2013-098461 dated May 1, 2014 (15 pages).
Japanese Office Action with English translation from Japanese application 2013-98461 dated May 12, 2014 (15 pages).
Japanese Office Action with English translation from Japanese application 2014-184926 dated Feb. 29, 2016 (13 pages).
Japanese Office Action with English translation from Japanese application 2014-184926 dated Jul. 6, 2015 (6 pages).
Jones and Dershem, "Synchrotron Radiation from Proton in a 20 TEV, 10 TESLA Superconducting Super Collider" Proceedings of the 12th International Conference on High-Energy Accelerator, Aug. 11-16, 1983, pp. 138-140.
Jones and Mills, "The South African National Accelerator Centre: Particle Therapy and Isotope Production Programmes," Radiation Physics and Chemistry, Apr.-Jun. 1998, 51 ( 4-6):571-578.
Jones et al., "Status Report of the NAC Particle Therapy Programme," Stralentherapie and Onkologie, vol. 175, Suppl. II, Jun. 1999, pp. 30-32.
Jones, "Present Status and Future Trends of Heavy Particle Radiotherapy," Cyclotrons and their Applications 1998, Proceedings of the Fifteenth International Conference on Cyclotrons and their Applications, Jun. 14-19, 1998, pp. 13-20.
Jones, "Progress with the 200 MeV Cyclotron Facility at the National Accelerator Centre," Commission of the European Communities Radiation Protection Proceedings, Fifth Symposium on Neutron Dosimetry, Sep. 17-21, 1984, vol. II, pp. 989-998.
Jong-Won Kim: "An eight Tesla superconducting magnet for cyclotron studies", Dissertation, Apr. 12, 2004 (Apr. 12, 2004), XP055187967, Retrieved from the Internet: URL:https://publications.nscl.msu.edu/thesis/Kim1994_85.pdf [retrieved on May 7, 2015] (138 pages).
Jongen et al., "Development of a Low-cost Compact Cyclotron System for Proton Therapy," National Institute of Radial. Sci,1991, No. 81, DD. 189-200.
Jongen et al., "Progress report on the IBA-SHI small cyclotron for cancer therapy" Nuclear Instruments and Methods in Physics Research, Section B, vol. 79, issue 1-4, 1993, pp. 885-889.
Jongen et al., "The proton therapy system for MGH's NPTC: equipment description and progress report," Bulletin du Cancer/Radiotherapie, Proceedings of the meeting of the European Heavy Particle Therapy Group, 1996, 83(Suppl. 1):219-222.
Jongen et al., "The proton therapy system for the NPTC: Equipment Description and progress report," Nuclear Instruments and methods in physics research, 1996, Section B, 113(1 ): 522-525.
Kanai et al., "Three-dimensional Beam Scanning for Proton Therapy," Nuclear Instruments and Methods in Physic Research, Sep. 1, 1983, The Netherlands, 214(23):491-496.
Karlin et al., "Medical Radiology" (Moscow), 1983, 28, 13.
Karlin et al., "The State and Prospects in the Development of the Medical Proton Tract on the Synchrocyclotron in Gatchina," Med. Radial., Moscow, 28(3):28-32 (Mar. 1983) (German with English Abstract on end of p. 32).
Kats and Druzhinin, "Comparison of Methods for Irradiation Prone Patients," Atomic Energy, Feb. 2003, 94(2): 120-123.
Kats and Onosovskii, "A Planar Magnetooptical System for the Irradiation of a Lying Patient with a Proton Beam from Various Directions," Instruments and Experimental Techniques, 1996, 39(1):127.
Kats and Onosovskii, "A Simple, Compact, Flat System for the Irradiation of a Lying Patient with a Proton Beam from Different Directions," Instruments and Experimental Techniques, 1996, 39(1): 132-134.

Khoroshkov et al.,"Moscow Hospital-Based Proton Therapy Facility Design," Am. Journal Clinical Oncology: CCT, Apr. 1994, 17(2)1 09-114.
Kim and Blosser, "Optimized Magnet for a 250 MeV Proton Radiotherapy Cyclotron," Cyclotrons and Their Applications 2001, May 2001, Sixteenth International Conference, pp. 345-347.
Kim and Yun, "A Light-Ion Superconducting Cyclotron System for Multi-Disciplinary Users," Journal of the Korean Physical Society, Sep. 2003, 43(3):325-331.
Kim et al., "Construction of 8T Magnet Test Stand for Cyclotron Studies," IEEE Transactions on Applied Superconductivity, Mar. 1993, 3(1):266-268.
Kim et al., "Design Study of a Superconducting Cyclotron for Heavy Ion Therapy," Cyclotrons and Their Applications 2001, Sixteenth International Conference, May 13-17, 2001, pp. 324-326.
Kim et al., "Trim Coil System for the Riken Cyclotron Ring Cyclotron," Proceedings of the 1997 Particle Accelerator Conference, IEEE, Dec. 1981, vol. 3, pp. 214-235 or 3422-3424, 1998.
Kim, J., An Eight Tesla Superconducting Magnet for Cyclotron Studies, Ph.D. Dissertation, Michigan State University, Department of Physics and Astronomy, 138 pages (1994), copy retrieved from the internet Apr. 12, 2004 <https://publications.nscl.msu.edu/thesis/Kim1994_85.pdf>.
Kimstrand, "Beam Modelling for Treatment Planning of Scanned Proton Beams," Digital Comprehensive Summaries of Uppsala dissertations from the Faculty of Medicine 330, Uppsala Universitet, 2008, 58 pages.
Kishida and Yano, "Beam Transport System for the RIKEN SSC (II)," Scientific Papers of the Institute of Physical and Chemical Research, Dec. 1981, 75(4):214-235.
Koehler et al., "Range Modulators for Protons and Heavy Ions," Nuclear Instruments and Methods, 1975, vol. 131, pp. 437-440.
Koto and Tsujii, "Future of Particle Therapy," Japanese Journal of Cancer Clinics, 2001, 47(1):95-98 [Lang.: Japanese], English abstract (htt12://sciencelinks.j12/ieast/article/200206/000020020601A0511453.php).
Kraft et al., "Hadrontherapy in Oncology," U. Amaldi and Larrsson, editors Elsevier Science, 1994, 390 pages.
Krevet et al., "Design of a Strongly Curved Superconducting Bending Magnet for a Compact Synchrotron Light Source," Advances in Cryogenic Engineering, 1988, vol. 33, pp. 25-32.
Laisne et al., "The Orsay 200 MeV Synchrocyclotron," IEEE Transactions on Nuclear Science, Apr. 1979, NS-26(2):1919-1922.
Larsson et al., Nature,1958, 182:1222.
Larsson, Biomedical Program for the Converted 200-MeV Synchrocyclotron at the Gustaf Werner Institute, Radiation Research, 1985, 104:S310-S318.
Lawrence et al., "Heavy particles in acromegaly and Cushing's Disease," in Endocrine and Norendocrine Hormone Producing Tumors (Year Book Medical Chicago, 1973, pp. 29-61.
Lawrence et al., "Successful Treatment of Acromegaly: Metabolic and Clinical Studies in 145 Patients," The Journal of Clinical Endrocrinology and Metabolism, Aug. 1970, 31(2), 21 pages.
Lawrence et al., "Treatment of Pituitary Tumors," Excerpta medica, Amsterdam/American Elsevier, New York, 1973, pp. 253-262.
Lawrence, J.H., Proton Irradiation of the Pituitary Cancer, vol. 10, pp. 795-798 (1957).
Lecroy et al., "Viewing Probe for High Voltage Pulses," Review of Scientific Instruments USA, Dec. 1960, 31(12):1354.
Lin et al., "Principles and 10 Year Experience of the Beam Monitor System at the PSI Scanned Proton Therapy Facility", Center for Proton Radiation Therapy, Paul Scherrer Institute, CH-5232, Villigen PSI, Switzerland, 2007, 21 pages.
Linfoot et al., "Acromegaly," in Hormonal Proteins and Peptides, edited by C.H. Li, 1975, pp. 191-246.
Literature Author and Keyword Search, dated Feb. 14, 2005, 44 pages.
Literature Keyword Search, dated Jan. 24, 2005, 98 pages.
Literature Search and Keyword Search for Synchrocyclotron, dated Jan. 25, 2005, 68 pages.
Literature Search by Company Name/Component Source, dated Jan. 24, 2005, 111 pages.
Literature Search, dated Jan. 26, 2005, 36 pages.

(56) References Cited

OTHER PUBLICATIONS

Livingston et al., "A capillary ion source for the cyclotron," Review Science Instruments, Feb. 1939, 10:63.
LLNL, UC Davis Team Up to Fight Cancer, Lawrence Livermore National Laboratory, Apr. 28, 2006, SF-06-04-02, Livermore, California, pp. 1-4.
Mandrillon, "High Energy Medical Accelerators," EPAC 90, 2nd European Particle Accelerator Conference, Jun. 12-16, 1990, 2:54-58.
Marchand et al., "IBA Proton Pencil Beam Scanning: an Innovative Solution for Cancer Treatment," Proceedings of EP AC 2000, Vienna, Austria, 3 pages.
Marti et al., "High Intensity Operation of a Superconducting Cyclotron," Proceedings of the 14th International Conference, Cyclotrons and Their Applications, Oct. 1995, pp. 45-48 (Oct. 1995).
Martin, "Operational Experience with Superconducting Synchrotron Magnets" Proceedings of the 1987 IEEE Particle Accelerator Conference, Mar. 16-19, 1987, vol. 3 of 3: 1379-1382.
Meote et al., "ETOILE Hadrontherapy Project, Review of Design Studies" Proceedings of EPAC 2002, 2002, pp. 2745-2747.
Miyamoto et al., "Development of the Proton Therapy System," The Hitachi Hyoron, 79(10):775-779 (1997) [Lang: Japanese], English abstract (http://www.hitachi.com/rev/1998/revfeb98/rev4 706.htm).
Montelius et al., "The Narrow Proton Beam Therapy Unit at the Svedberg Laboratory in Uppsala," ACTA Oncologica, 1991, 30:739-745.
Moser et al., "Nonlinear Beam Optics with Real Fields in Compact Storage Rings," Nuclear Instruments & Methods in Physics Research/Section B, B30, Feb. 1988, No. 1, pp. 105-109.
Moyers et al., "A Continuously Variable Thickness Scatterer for Proton Beams Using Self-compensating Dual Linear Wedges" Loma Linda University Medical Center, Dept. of Radiation Medicine, Loma Linda, CA, Nov. 2, 1992, 21 pages.
National Cancer Institute Funding (Senate-Sep. 21, 1992) (www.thomas.loc.gov/cgi-bin/query/z?r102:S21SE2-712 (2 pages).
Nicholson, "Applications of Proton Beam Therapy," Journal of the American Society of Radiologic Technologists, May/Jun. 1996, 67(5): 439-441.
Nolen et al., "The Integrated Cryogenic—Superconducting Beam Transport System Planned for MSU," Proceedings of the J21h International Conference on High-Energy Accelerators, Aug. 1983, pp. 549-551.
Non-Final Office Action with English translation from Japanese Patent Office 2010-536131, dated Jun. 4, 2013 (10 pages).
Norimine et al., "A Design of a Rotating Gantry with Easy Steering for Proton Therapy," Proceedings of EPAC 2002, 2002, pp. 2751-2753.
Office action from Canadian Application 2629333 dated Aug. 30, 2010 (5 pages).
Office action from European Application 11177602.7 dated Jun. 1, 2015 (5 pages).
Office action from European Application 11177603.5 dated Jun. 27, 2013 (5 pages).
Office action from European application 11177605.0 dated Jun. 27, 2013 (5 pages).
Office action from European application 11177606.8 dated Jun. 27, 2013 (5 pages).
Office action from European application 11177607.6 dated Jun. 27, 2013 (6 pages).
Office action dated Mar. 3, 2014 from Japanese application No. 2013-45084 (5 pages).
Office action dated Mar. 3, 2014 from Japanese application No. 2013-45085 (5 pages).
Office action with English translation from Chinese application 200680051421.0 dated Dec. 25, 2009 (9 pages).
Office action with English translation from Japanese application 2013-45084 dated Mar. 3, 2014 (6 pages).
Office action with English translation from Japanese application 2013-45085 dated Mar. 3, 2014 (6 pages).
Office action with English translation from Taiwanese application 097144550 dated Oct. 21, 2013 (17 pages).
Ogino, Takashi, "Heavy Charged Particle Radiotherapy-Proton Beam", Division of Radiation Oncology, National Cancer Hospital East, Kashiwa, Japan, Dec. 2003, 7 pages.
Okumura et al., "Overview and Future Prospect of Proton Radiotherapy," Japanese Journal of.
Okumura et al., "Proton Radiotherapy" Japanese Journal of Cancer and Chemotherapy, 1993, 10.
Outstanding from Search Reports, "Accelerator of Polarized Portons at Fermilab," 2005, 20 pages.
Paganetti et al., "Proton Beam Radiotherapy—The State of the Art," Springer Verlag, Heidelberg, ISBN 3-540-00321-5, Oct. 2005,36 pages.
Palmer and Tollestrup, "Superconducting Magnet Technology for Accelerators," Annual Review of Nuclear and Particle Science, 1984, vol. 34, pp. 247-284.
Patent Assignee and Keyword Searches for Synchrocyclotron, dated Jan. 25, 2005, 78 pages.
Patent Assignee Search Paul Scherrer Institute, Library Services at Fish & Richardson P.C., dated Mar. 20, 2007, 40 pages.
Patent Prior Art Search for 'Proton Therapy System', Library Services at Fish & Richardson P.C., dated Mar. 20, 2007, 46 pages.
Pavlovic, "Beam-optics study of the gantry beam delivery system for light-ion cancer therapy," Nuclear Instruments and Methods in Physics Research, Section A, Nov. 1997, 399(2):439-454(16).
Pedroni and Enge, "Beam optics design of compact gantry for proton therapy" Medical & Biological Engineering & Computing, May 1995, 33(3):271-277.
Pedroni and Jermann, . "SGSMP: Bulletin Mar. 2002 Proscan Project, Progress Report on the PROSCAN Project of PSI" [online] retrieved from www.sgsmp.ch/protA23.htm, Mar. 2002, 5 pages.
Pedroni et al., "A Novel Gantry for Proton Therapy at the Paul Scherrer Institute," Cycloctrons and Their Applications 2001: Sixteenth International Conference. AIP Conference Proceedings, 2001, 600:13-17.
Pedroni et al., "The 200-MeV proton therapy project at the Paul Scherrer Institute: Conceptual design and practical realization," Medical Physics, Jan. 1995, 22(1):37-53.
Pedroni, "Accelerators for Charged Particle Therapy: Performance Criteria from the User Point of View," Cyclotrons and their Applications, Proceedings of the 13th International Conference, Jul. 6-10, 1992, pp. 226-233.
Pedroni, "Latest Developments in Proton Therapy" Proceedings of EPAC 2000, 2000, pp. 240.
Pedroni, "Status of Proton Therapy: results and future trends," Paul Scherrer Institute, Division of.
Peggs et al., "A Survey of Hadron Therapy Accelerator Technologies," Particle Accelerator Conference, Jun. 25-29, 2007, 7 pages.
Potts et al., "MPWP6-Therapy III: Treatment Aids and Techniques" Medical Physics, Sep./Oct. 1988, 15(5):798.
Pourrahimi et al., "Powder Metallurgy Processed Nb3Sn(Ta) Wire for High Field NMR magnets," IEEE Transactions on Applied Superconductivity, Jun. 1995, 5(2)1 603-1606.
Prieels et al., "The IBA State-of-the-Art Proton Therapy System, Performances and Recent Results," Application of Accelerators in Research and industry—Sixteenth Int'l Conj, American Institute of Physics, Nov. 1-5, 2000, 576:857-860.
Rabin et al., "Compact Designs for Comprehensive Proton Beam Clinical Facilities," Nuclear Instruments & Methods in Physics Research, Apr. 1989, Section B, vol. 40-41, Part II, pp. 1335-1339.
Radiation Medicine, 1994, 5 pages.
Research & Development Magazine. "Proton Thern11v Center Nearing Completion," Aug. 1999, 41(9):2 pages, (www.rdmag.com).
Resmini, "Design Characteristics of the K=800 Superconducting Cyclotron at M.S.U.," Cyclotron Laboratory, Michigan State University, East Lansing, Michigan 48824, IEEE Transaction on Nuclear Science, vol. NS-26, No. 2, Apr. 1979, 8 pages.
Response to Canadian Office action dated May 1, 2014 in Canadian Application 2707012 filed on Oct. 30, 2014 (14 pages).

(56) References Cited

OTHER PUBLICATIONS

Response to Chinese office action with English translation from Chinese application 200780102281.X dated Dec. 7, 2011, filed Jun. 21, 2012 (27 pages).
Response to Chinese office action with English translation from Chinese application 200780102281.X dated Oct. 23, 2012, filed Mar. 7, 2013 (26 pages).
Response to European office action from European application 07868958.5 dated Jul. 16, 2010, filed on Aug. 26, 2010 (9 pages).
Response to European office action from European application 11165422.4 dated Apr. 17, 2012, filed Oct. 17, 2012 (15 pages).
Response to European office action from European application 11165423.2 dated Sep. 2, 2011, filed Mar. 2, 2012 (15 pages).
Response to European office action from European application 12193833.6 dated Mar. 27, 2013, filed Sep. 25, 2013 (23 pages).
Response to European office action from European application 12193850.0 dated Feb. 24, 2015, filed on Mar. 4, 2015 (9 pages).
Response to European office action from European application 12193850.0 dated Jul. 2, 2013, filed on Oct. 17, 2013 (28 pages).
Response to European office action from European application 12193850.0 dated Mar. 18, 2015, filed Apr. 29, 2015 (10 pages).
Response to Examination Report from European Application No. 06838033.6 dated Jan. 7, 2014 (17 pages).
Response to Examination Report from European Application No. 11177602.7 dated Oct. 3, 2013 (7 pages).
Response to Examination Report from European Application No. 11177607.6 dated Jan. 7, 2014 (15 pages).
Response to Japanese office action dated May 1, 2014 in Japanese application 2013-098461 filed on Sep. 11, 2014 (23 pages).
Response to Japanese office action with English translation from Japanese application 2010535942 dated Jun. 19, 2012, filed on Sep. 14, 2012 (14 pages).
Response to office action dated Jun. 27, 2013 in European application No. 11177607.6 filed on Jan. 7, 2014 (15 pages).
Response to office action dated Mar. 27, 2013 in European application 11177602.7 filed on Oct. 3, 2013 (7 pages).
Response to office action with English translation from Chinese application 200680051421.0 filed on Jun. 24, 2010 (32 pages).
Response to office action with English translation from Japanese application 2013-45084 filed on May 27, 2014 (12 pages).
Response to office action with English translation from Japanese application 2013-45085 filed on May 24, 2014 (14 pages).
Response to office action with English translation from Taiwanese application 097144550 filed on Apr. 18, 2014 (10 pages).
Response to Summons to attend oral proceeding pursuant to Rule 115(1) EPC from European application 11177607.6 dated Jun. 11, 2015, filed Jan. 25, 2016 (30 pages).
Response with English translation to Japanese Office action from Japanese application 201398461 dated May 12, 2014, filed on Sep. 11, 2014 (24 pages).
Response with English translation to Japanese Office action from Japanese application 2014184926 dated Jul. 6, 2015, filed on Oct. 6, 2015 (12 pages).
RetroSearch "Berkeley 88-Inch Cyclotron 'RF' or 'Frequency Control'," Jan. 21, 2005, 36 pages.
RetroSearch "Berkeley 88-Inch Cyclotron," Jan. 24, 2005, 170 pages.
RetroSearch "Bernard Gottschalk, Cyclotron, Beams, Compensated Upstream Modulator, Compensated Scatter," Jan. 21, 2005, 20 pages.
RetroSearch "Cyclotron with 'RF' or 'Frequency Control'," Jan. 21, 2005, 49 pages.
RetroSearch Gottschalk, Bernard, Harvard Cyclotron Wheel, Jan. 21, 2005, 20 pages.
RetroSearch "Loma Linda University Beam Compensation," Jan. 21, 2005, 60 pages.
RetroSearch "Loma Linda University, Beam Compensation Foil Wedge," Jan. 21, 2005, 15 pages.
Revised Patent Keyword Search, dated Jan. 25, 2005, 88 pages.
Rifuggiato et, al., "Status Report of the LNS Superconducting Cyclotron" Nukleonika, 2003, 48:SI31-SI34, Supplement 2.
Rode, "Tevatron Cryogenic System," Proceedings of the 12th International Conference on High-energy Accelerators, Fermilab, Aug. 11-16, 1983, pp. 529-535.
Salzburger et al., "Superconducting Synchrotron Magnets Supraleitende Synchrotronmagnete," Siemens A.G., Erlangen (West Germany). Abteilung Technische Physik, Report No. BMFT-FB-T-75-25, Oct. 1975, p. 147, Journal Announcement: GRAI7619; STAR1415, Subm-Sponsored by Bundesmin. Fuer Forsch. U. Technol. In German; English Summary.
Schillo et al,. "Compact Superconducting 250 MeV Proton Cyclotron for the PSI Proscan Proton Therapy Project," Cyclotrons and Their Applications 2001, Sixteenth International Conference, 2001, pp. 37-39.
Schneider et al., "Nevis Synchrocyclotron Conversion Program—RF System," IEEE Transactions on Nuclear Science USA, Jun. 1969, ns. 16(3): 430-433.
Schneider et al., "Superconducting Cyclotrons," IEEE Transactions on Magnetics, vol. MAG-11, No. 2, Mar. 1975, New York, pp. 443-446.
Schreuder et al., "The Non-orthogonal Fixed Beam Arrangement for the Second Proton Therapy Facility at the National Accelerator Centre," Application of Accelerators in Research and Industry, American Institute of Physics, Proceedings of the Fifteenth International Conference, Nov. 1998, Part Two, pp. 963-966.
Schreuder, "Recent Developments in Superconducting Cyclotrons," Proceedings of the 1995 Particle Accelerator Conference, May 1-5, 1995, vol. 1, pp. 317-321.
Schubert and Blosser, "Conceptual Design of a High Field Ultra-Compact Cyclotron for Nuclear Physics Research," Proceedings of the 1997 Particle Accelerator Conference, May 12-16, 1997, vol. 1, 3 pp. 1060-1062.
Schubert, "Extending the Feasibility Boundary of the Isochronous Cyclotron," Dissertation submitted to Michigan State University, 1997, Abstract http://adsabs.harvard.edu/abs/1998PhDT . . . 147S.
Second Office Action (English translation) for JP2014-184926, 6 pages (dated Jan. 30, 2017).
Second Office Action (Japanese translation) for JP2014-184926, 5 pages (dated Jan. 30, 2017).
Shelaev et al., "Design Features of a Model Superconducting Synchrotron of JINR," Proceedings of the 12th International Conference on High-energy Accelerators, Aug. 11-16, 1983, pp. 416-418.
Shintomi et. Al, "Technology and Materials for the Superconducting Super Collider (SSC) Project," [Lang.: Japanese], The Iron and Steel Institute of Japan 00211575, 78(8): 1305-1313, 1992, http://ci.nii.ac.jp/naid/110001493249/en/.
Sisterson, "Clinical use of proton and ion beams from a world-wide perspective," Nuclear Instruments and Methods in Physics Research, Section B, 1989, 40-41:1350-1353.
Sisterson, "World Wide Proton Therapy Experience in 1997," The American Insitute of Physics, 910 Applications of Accelerators in Research and Industry, Proceedings of the Fifteenth International Conference, Part Two, Nov. 1998, pp. 959-962.
Slater et al., "Developing a Clinical Proton Accelerator Facility: Consortium-Assisted Technology Transfer," Conference Record of the 1991 IEEE Particle Accelerator Conference: Accelerator Science and Technology, vol. 1, May 6-9, 1991, pp. 532-536.
Slater et al., "Development of a Hospital-Based Proton Beam Treatment Center," International Journal of Radiation Oncology Biology Physics, Apr. 1988, 14(4):761-775.
Smith et al., "The Northeast Proton Therapy Center at Massachusetts General Hospital" Journal of Brachytherapy International, Jan. 1997, pp. 137-139.
Snyder and Marti, "Central region design studies for a proposed 250 MeV proton cyclotron," Nuclear Instruments and Methods in Physics Research, Section A, 1995, vol. 355, pp. 618-623.
Soga, "Progress of Particle Therapy in Japan," Application of Accelerators in Research and Industry, American Institute of Physics, Sixteenth International Conference, Nov. 2000, pp. 869-872.

(56) References Cited

OTHER PUBLICATIONS

Spiller et al., "The GSI Synchrotron Facility Proposal for Acceleration of High Intensity Ion and Proton Beams" Proceedings of the 2003 Particle Accelerator Conference, May 12-16, 2003, vol. 1, pp. 589-591.
Stanford et al., "Method of Temperature Control in Microwave Ferroelectric Measurements," Sperry Microwave Electronics Company, Clearwater, Florida, Sep. 19, 1960, 1 page.
Summons to attend oral proceeding pursuant to Rule 115(1) EPC from European application 11177607.6 dated Jun. 11, 2015 (5 pages).
Superconducting Cyclotron Contract awarded by Paul Scherrer Institute (PSI), Villigen, Switzerland, http://www.accel.de/News/superconducting_ cyclotron_ contract.htm, Jan. 2009, 1 page.
Tadashi et al., "Large superconducting super collider (SSC) in the planning and materials technology," 1992, 78(8):1305-1313, The Iron and Steel Institute of Japan 00211575.
Takada, "Conceptual Design of a Proton Rotating Gantry for Cancer Therapy," Japanese Journal of Medical Physics, 1995, 15(4):270-284.
Takayama et al., "Compact Cyclotron for Proton Therapy," Proceedings of the 8lh Symposium on Accelerator Science and Technology, Japan, Nov. 25-27, 1991, pp. 380-382.
Teng, "The Fermilab Tevatron," Coral Gables 1981, Proceedings, Gauge Theories, Massive Neutrinos, and Proton Decay, 1981, pp. 43-62.
The Davis 76-Inch Isochronous Cyclotron, Beam On: Crocker Nuclear Laboratory, University of California, 2009, 1 page.
The Journal of Practical Pharmacy, 1995, 46(1):97-103 [Japanese].
The K250 Proton therapy Cyclotron, National Superconducting Cyclotron Laboratory at Michigan State University (NSCL), retrieved from: http://www.nscl.msu.edu/tech/accelerators/k250.html, Feb. 2005, 2 pages.
The KlOO Neutron-therapy Cyclotron, National Superconducting Cyclotron Laboratory at Michigan State University (NSCL ), retrieved from: http://www.nscl.msu.edu/tech/accelerators/k100, Feb. 2005, 1 page.
Tilly et al., "Development and verification of the pulsed scanned proton beam at The Svedberg Laboratory in Uppsala," Phys. Med. Biol., 2007, 52:2741-2754.
Tobias, C.A., et al., Pituitary Irradiation with High-Energy Proton Beams a Preliminary Report, Cancer Research, vol. 18, No. 2, pp. 121-134 (1958).
Torn, "The Use of Compact Cyclotrons for Producing Fast Neutrons for Therapy in a Rotatable Isocentric Gantry," IEEE Transaction on Nuclear Science, Apr. 1979, 26(2):2294-2298.
Toyoda, "Proton Therapy System", Sumitomo Heavy Industries, Ltd., 2000, 5 pages.
Trinks et. al., "The Tritron: A Superconducting Separated-Orbit Cyclotron," Nuclear Instruments and Methods in Physics Research, Section A, 1986, vol. 244, pp. 273-282.
Tsuji, "The Future and Progress of Proton Beam Radiotherapy," Journal of Japanese Society for Therapeutic Radiology and Oncology, 1994, 6(2):63-76.
UC Davis School of Medicine, "Unlikely Partners Turn Military Defense into Cancer Offense", Current Issue Summer 2008, Sacramento, California, pp. 1-2.

Umegaki et al., "Development of an Advanced Proton Beam Therapy System for Cancer Treatment" Hitachi Hyoron, 2003, 85(9):605-608 [Lang.: Japanese], English abstract, http://www.hitachi.com/ICSFiles/afieldfile/2004/06/0I/r2003_04_104.pdf or http://www.hitachi.com/rev/archive/2003/2005649_12606.html (full text) [Hitachi, 52(4), Dec. 2003].
Umezawa et al., "Beam Commissioning of the new Proton Therapy System for University of Tsukuba," Proceedings of the 2001 Particle Accelerator Conference, vol. 1, Jun. 18-22, 2001, pp. 648-650.
van Steenbergen, "Superconducting Synchroton Development at BNL," Proceedings of the 8th International Conference on High-Energy Accelerators CERN 1971, 1971, pp. 196-198.
van Steenbergen, "The CMS, a Cold Magnet Synchrotron to Upgrade the Proton Energy Range of the BNL Facility," IEEE Transactions on Nuclear Science, Jun. 1971, 18(3):694-698.
Vandeplassche et al., "235 MeV Cyclotron for MGH's Northeast Proton Therapy Center (NPTC): Present Status," EPAC 96, Fifth European Partical Accelerator Conference, vol. 3, Jun. 10-14, 1996, pp. 2650-2652.
Voluntary Amendment filed Nov. 27, 2013 in Chinese application No. 201310049231.7 (16 pages).
Vorobiev et al., "Concepts of a Compact Achromatic Proton Gantry with a Wide Scanning Field", Nuclear Instruments and Methods in Physics Research, Section A., 1998, 406(2):307-310.
Vrenken et al., "A Design of a Compact Gantry for Proton Therapy with 2D-Scanning," Nuclear Instruments and Methods in Physics Research, Section A, 1999, 426(2):618-624.
Wikil2edia, "Cyclotron" http://en.wikil2edia.org/wiki/Cyclotron (originally visited Oct. 6, 2005, revisited Jan. 28, 2009). 7 pages.
Wikipedia, "Synchrotron" htt12://en.wikil2edia.org/wiki/Synchrotron (originally visited Oct. 6, 2005. revisited Jan. 28, 2009). 7 pages.
Worldwide Patent Assignee Search, dated Jan. 24, 2005, 224 pages.
Worldwide Patent Keyword Search, dated Jan. 24, 2005, 94 pages.
Wu, "Conceptual Design and Orbit Dynamics in a 250 MeV Superconducting Synchrocyclotron," Ph.D. Dissertation, Michigan State University, Department of Physics and Astronomy, 1990, 172 pages.
York et al., "Present Status and Future Possibilities at NSCL-MSU," EP AC 94, Fourth European Particle Accelerator Conference, pp. 554-556, Jun. 1994.
York et al., "The NSCL Coupled Cyclotron Project—Overview and Status," Proceedings of the Fifteenth International Conference on Cyclotrons and their Applications, Jun. 1998, pp. 687-691.
Yudelev et al., "Hospital Based Superconducting Cyclotron for Neutron Therapy: Medical Physics Perspective," Cyclotrons and their applications 2001, 16th International Conference. American Institute of Physics Conference Proceedings, vol. 600, May 13-17, 2001, pp. 40-43.
Zherbin et al., "Proton Beam Therapy at the Leningrad Synchrocyclotron (Clinicomethodological Aspects and Therapeutic Results)", Aug. 1987, 32(8):17-22, (German with English abstract on pp. 21-22).
First Office Action for JP2016-129943 (English translation), 6 pages (dated Jun. 19, 2017).
First Office Action for JP2016-129943 (Japanese translation), 4 pages (dated Jun. 19, 2017).
Office Action for U.S. Appl. No. 15/266,372, 36 pages (dated May 11, 2017).

\* cited by examiner

INNER GANTRY

CROSS-REFERENCE TO RELATED APPLICATIONS

This patent application is a continuation of U.S. patent application Ser. No. 14/542,966, entitled "Inner Gantry" and filed on Nov. 17, 2014, which is a continuation of U.S. patent application Ser. No. 13/532,530, entitled "Inner Gantry" and filed on Jun. 25, 2012(issued as U.S. Pat. No. 8,916,843 on Dec. 23, 2014), which is a continuation of U.S. patent application Ser. No. 12/275,103, entitled "Inner Gantry" and filed on Nov. 20, 2008 (issued as U.S. Pat. No. 8,344,340 on Jan. 1, 2013), which is a continuation-in-part of U.S. patent application Ser. No. 11/601,056, entitled "Charged Particle Radiation Therapy" and filed on Nov. 17, 2006 (issued as U.S. Pat. No. 7,728,311 on Jun. 1, 2010), and therefore this application also entitled to the benefit of the filing date of U.S. Provisional Application No. 60/738,404, entitled "Charged Particle Radiation Therapy" and filed on Nov. 18, 2005. This application is also entitled to the benefit of the filing date of U.S. Provisional Application No. 60/991,454, entitled "Inner Gantry" and filed on Nov. 30, 2007. The contents of U.S. patent application Ser. Nos. 14/542,966, 13/532,530, 12/275,103, 11/601,056, and of U.S. Provisional Applications Nos. 60/991,454 and 60/738,404, are hereby incorporated by reference into this application as if set forth herein in full. This application also shares a common priority with U.S. application Ser. No. 13/303,110 (issued as U.S. Pat. No. 8,907,311 on Dec. 9, 2014), the contents of which are also incorporated herein by reference.

TECHNICAL FIELD

This patent application describes an inner gantry for use with a particle beam therapy system.

BACKGROUND

The design of a proton or ion radiation therapy system for a clinical environment should take account of overall size, cost, and complexity. Available space is usually limited in crowded clinical environments. Lower cost allows more systems to be deployed to reach a broader patient population. Less complexity reduces operating costs and makes the system more reliable for routine clinical use.

Other considerations may also bear on the design of such a therapy system. By configuring the system to apply the treatment to patients who are held in a stable, reproducible position (for example, lying supine on a flat table), the physician can more precisely relocate the intended target, relative to the patient's anatomy, at each treatment. Reliable reproduction of the patient's position for each treatment also can be aided using custom molds and braces fitted to the patient. With a patient in a stable, fixed position, the radiotherapy beam can be directed into the patient from a succession of angles, so that, over the course of the treatment, the radiation dose at the target is enhanced while the extraneous radiation dose is spread over non-target tissues.

Traditionally, an isocentric gantry is rotated around the supine patient to direct the radiation beam along successive paths that lie at a range of angles in a common vertical plane toward a single point (called an isocenter) within the patient. By rotating the table on which the patient lies around a vertical axis, the beam can be directed into the patient along different paths. Other techniques have been used to vary the position of the radiation source around the patient, including robotic manipulation.

SUMMARY

In general, this patent application describes a system comprising a patient support and an outer gantry on which an accelerator is mounted. The outer gantry enables the accelerator to move through a range of positions around a patient on the patient support. The accelerator is configured to produce a proton or ion beam having an energy level sufficient to reach a target in the patient. An inner gantry comprises an aperture for directing the proton or ion beam towards the target. The system described above may include one or more of the following features, either alone or in combination.

The inner gantry may comprise an applicator for holding the aperture. The applicator may be movable along the inner gantry. The applicator may be configured to move the aperture relative to the patient. For example, the applicator may be configured to move the aperture towards, or away from, the patient.

The inner gantry may comprise a track along which the applicator is configured to move. A cover may be movable relative to the track. The cover may be for preventing objects from falling into a vault below the patient support.

A processing device may be programmed to control movement of the outer gantry and/or the inner gantry. The processing device may be configured to control movement of the outer gantry and/or the inner gantry to substantially align the proton or ion beam with the aperture. The aperture may be configured to substantially collimate the proton or ion beam. The system may comprise a patient support that is movable relative to the inner gantry and/or the outer gantry.

In general, this patent application also describes a system comprising a patient support and a gantry on which a particle beam accelerator is mounted. The particle beam accelerator is for directing a particle beam towards the patient support. The gantry is movable to positions above and below the patient support. An aperture is located between the particle beam accelerator and the patient support. The aperture is for modifying the particle beam. The system described above may include one or more of the following features, either alone or in combination.

The system may comprise an apparatus to hold the aperture. The apparatus may be movable relative to the patient support. The apparatus may comprise a robotic arm that is computer controlled to position the aperture relative to the patient support. The apparatus may comprise a stand, which is manually positionable, to hold the aperture.

The particle beam accelerator may be a synchrocyclotron. The system may comprise a second gantry that includes an applicator to hold the aperture. The second gantry may be controlled to substantially align the aperture with the particle beam.

In general, this patent application also describes a system comprising a patient support, a first gantry that is angularly movable relative to the patient support, and a particle accelerator that is mounted on the first gantry. The particle accelerator is configured to provide a particle beam directly towards the patient support. A second gantry is positioned relative to the patient support. The second gantry is substantially C-shaped. The system described above may include one or more of the following features, either alone or in combination.

The second gantry may comprise a track, an aperture, and an applicator. The applicator may be movable along the track so that the aperture is substantially aligned with the particle beam. The aperture may alter the particle beam before the particle beam reaches a patient on the patient support.

The system may comprise a computer to control the first gantry and the second gantry. The first gantry may be movable so that the particle accelerator is in a position above the patient support to a position below the patient support. The second gantry may comprise a cover to protect the particle accelerator when the particle accelerator is in the position below the patient support. The inner gantry may comprise a device to alter a size and/or shape of the particle beam. The device for altering the particle beam may be movable relative to the synchrocyclotron.

Any of the foregoing features may be combined to form implementations not specifically described herein.

The details of one or more examples are set forth in the accompanying drawings and the description below. Further features, aspects, and advantages will become apparent from the description, the drawings, and the claims.

DETAILED DESCRIPTION

Figure 1:
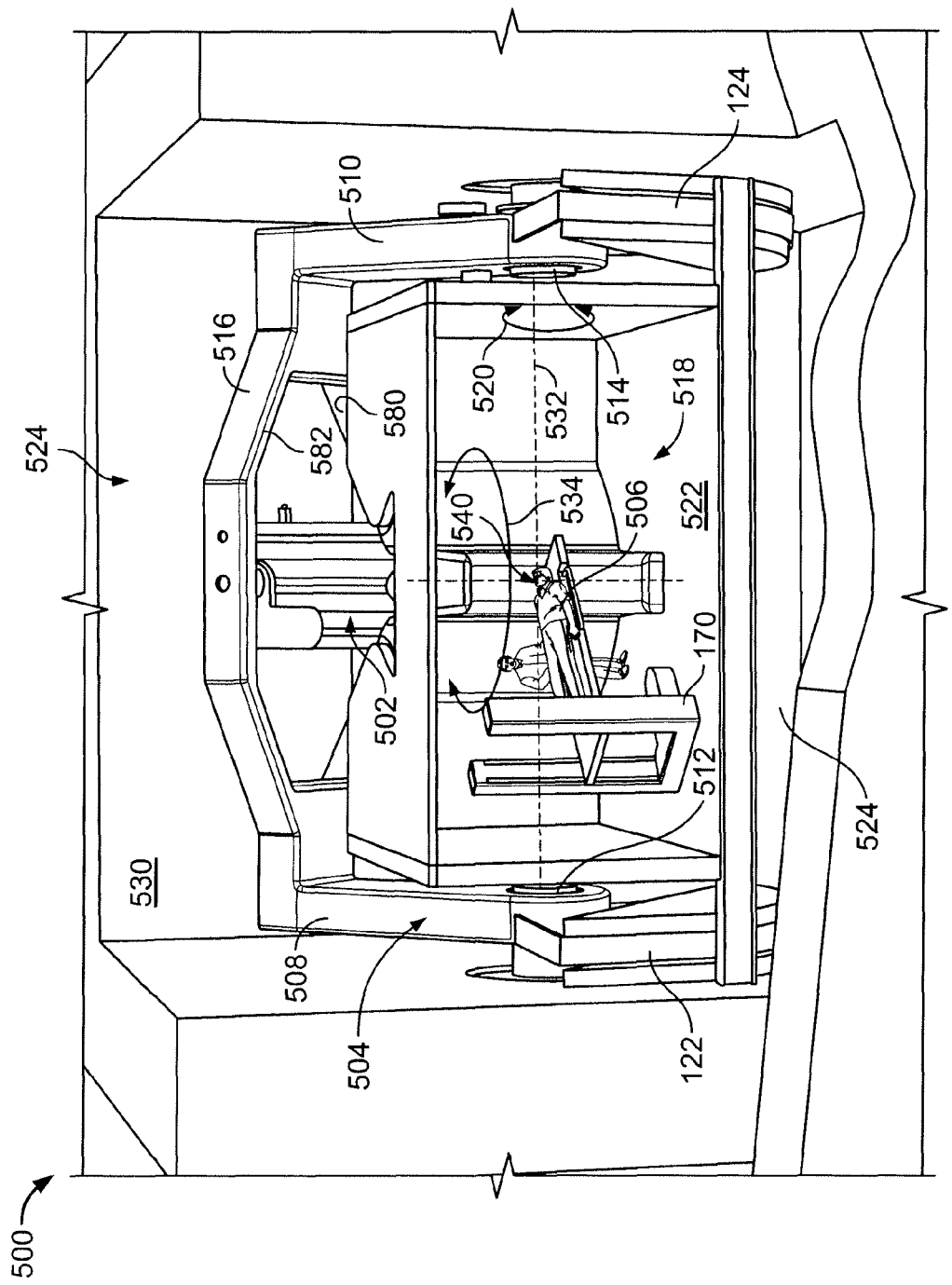
FIG. 1 is a perspective view of a therapy system.
Figure 2:
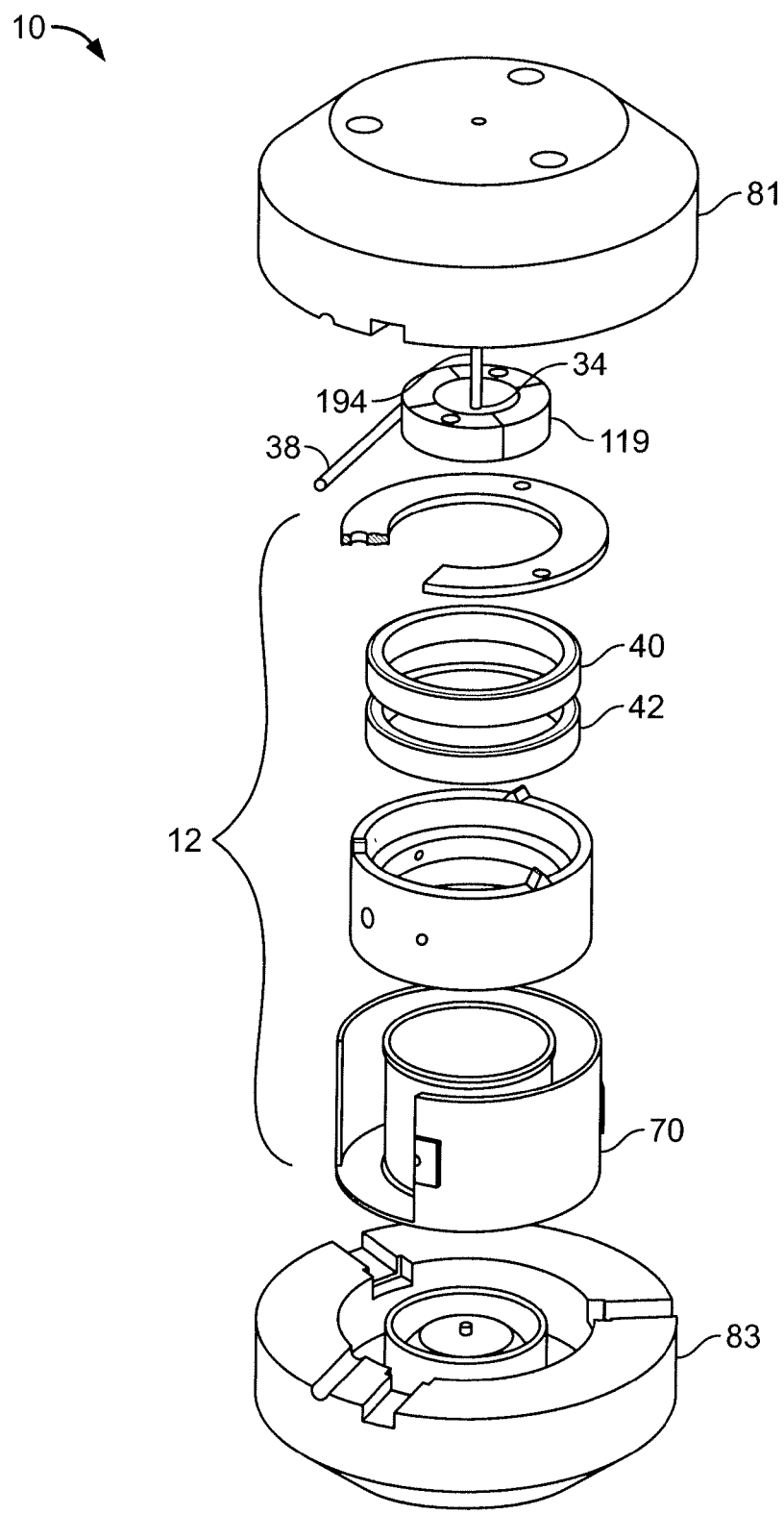
FIG. 2 is an exploded perspective view of components of a synchrocyclotron.

As shown in FIG. 1, a charged particle radiation therapy system 500 includes a beam-producing particle accelerator 502 having a weight and size small enough to permit it to be mounted on a rotating gantry 504 with its output directed straight (that is, essentially directly) from the accelerator housing toward a patient 506.

In some implementations, the steel gantry has two legs 508, 510 mounted for rotation on two respective bearings 512, 514 that lie on opposite sides of the patient. The accelerator is supported by a steel truss 516 that is long enough to span a treatment area 518 in which the patient lies (e.g., twice as long as a tall person, to permit the person to be rotated fully within the space with any desired target area of the patient remaining in the line of the beam) and is attached stably at both ends to the rotating legs of the gantry.

In some examples, the rotation of the gantry is limited to a range 520 of less than 360 degrees, e.g., about 180 degrees, to permit a floor 522 to extend from a wall of the vault 524 that houses the therapy system into the patient treatment area. The limited rotation range of the gantry also reduces the required thickness of some of the walls (which never directly receive the beam, e.g., wall 530), which provide radiation shielding of people outside the treatment area. A range of 180 degrees of gantry rotation is enough to cover all treatment approach angles, but providing a larger range of travel can be useful. For example the range of rotation may be between 180 and 330 degrees and still provide clearance for the therapy floor space.

The horizontal rotational axis 532 of the gantry is located nominally one meter above the floor where the patient and therapist interact with the therapy system. This floor is positioned about 3 meters above the bottom floor of the therapy system shielded vault. The accelerator can swing under the raised floor for delivery of treatment beams from below the rotational axis. The patient couch moves and rotates in a substantially horizontal plane parallel to the rotational axis of the gantry. The couch can rotate through a range 534 of about 270 degrees in the horizontal plane with this configuration. This combination of gantry and patient rotational ranges and degrees of freedom allow the therapist to select virtually any approach angle for the beam. If needed, the patient can be placed on the couch in the opposite orientation and then all possible angles can be used.

In some implementations, the accelerator uses a synchrocyclotron configuration having a very high magnetic field superconducting electromagnetic structure. Because the bend radius of a charged particle of a given kinetic energy is reduced in direct proportion to an increase in the magnetic field applied to it, the very high magnetic field superconducting magnetic structure permits the accelerator to be made smaller and lighter. The synchrocyclotron uses a magnetic field that is uniform in rotation angle and falls off in strength with increasing radius. Such a field shape can be achieved regardless of the magnitude of the magnetic field, so in theory there is no upper limit to the magnetic field strength (and therefore the resulting particle energy at a fixed radius) that can be used in a synchrocyclotron.

Certain superconducting materials begin to lose their superconducting properties in the presence of very high magnetic fields. High performance superconducting wire windings are used to allow very high magnetic fields to be achieved.

Superconducting materials typically need to be cooled to low temperatures for their superconducting properties to be realized. In some examples described here, cryo-coolers are used to bring the superconducting coil windings to temperatures near absolute zero. Using cryo-coolers can reduce complexity and cost.

The synchrocyclotron is supported on the gantry so that the beam is generated directly in line with the patient. The gantry permits rotation of the cyclotron about a horizontal rotational axis that contains a point (isocenter 540) within, or near, the patient. The split truss that is parallel to the rotational axis, supports the cyclotron on both sides.

Because the rotational range of the gantry is limited, a patient support area can be accommodated in a wide area around the isocenter. Because the floor can be extended broadly around the isocenter, a patient support table can be positioned to move relative to and to rotate about a vertical axis 542 through the isocenter so that, by a combination of gantry rotation and table motion and rotation, any angle of beam direction into any part of the patient can be achieved. The two gantry arms are separated by more than twice the height of a tall patient, allowing the couch with patient to rotate and translate in a horizontal plane above the raised floor.

Limiting the gantry rotation angle allows for a reduction in the thickness of at least one of the walls surrounding the treatment room. Thick walls, typically constructed of concrete, provide radiation protection to individuals outside the treatment room. A wall downstream of a stopping proton beam may be about twice as thick as a wall at the opposite end of the room to provide an equivalent level of protection. Limiting the range of gantry rotation enables the treatment room to be sited below earth grade on three sides, while allowing an occupied area adjacent to the thinnest wall reducing the cost of constructing the treatment room.

In the example implementation shown in FIG. 1, the superconducting synchrocyclotron 502 operates with a peak magnetic field in a pole gap of the synchrocyclotron of 8.8 Tesla. The synchrocyclotron produces a beam of protons having an energy of 250 MeV. In other implementations the field strength could be in the range of 6 to 20 Tesla and the proton energy could be in the range of 150 to 300 MeV The radiation therapy system described in this example is used for proton radiation therapy, but the same principles and details can be applied in analogous systems for use in heavy ion (ion) treatment systems.

As shown in FIGS. 2, 3, 4, 5, and 6, an example synchrocyclotron 10 (502 in FIG. 1) includes a magnet system 12 that contains an ion source 90, a radiofrequency drive system 91, and a beam extraction system 38. The magnetic field established by the magnet system has a shape appropriate to maintain focus of a contained proton beam using a combination of a split pair of annular superconducting coils 40, 42 and a pair of shaped ferromagnetic (e.g., low carbon steel) pole faces 44, 46.

Figure 7:
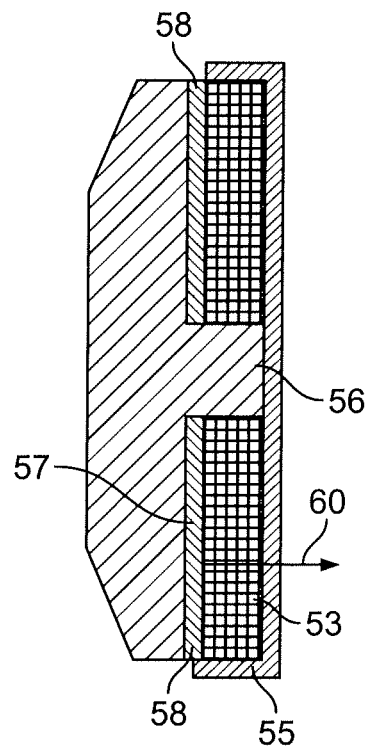
FIG. 7 is a cross-sectional view of a portion of a reverse bobbin and windings.
Figure 8:
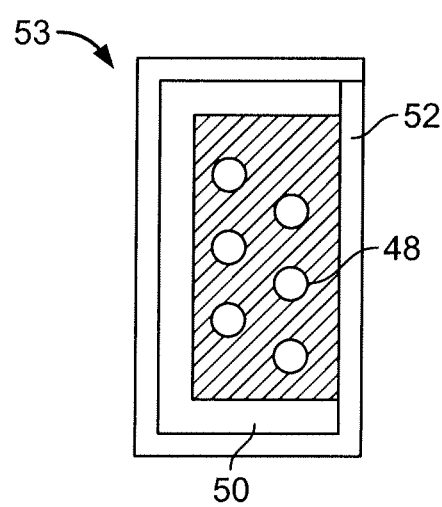
FIG. 8 is a cross sectional view of a cable-in-channel composite conductor.

The two superconducting magnet coils are centered on a common axis 47 and are spaced apart along the axis. As shown in FIGS. 7 and 8, the coils are formed by of Nb3Sn-based superconducting 0.6 mm diameter strands 48 (that initially comprise a niobium-tin core surrounded by a copper sheath) deployed in a Rutherford cable-in-channel conductor geometry. After six individual strands are laid in a copper channel 50, they are heated to cause a reaction that forms the final (brittle) material of the winding. After the material has been reacted, the wires are soldered into the copper channel (outer dimensions 3.02×1.96 mm and inner dimensions 2.05×1.27 mm) and covered with insulation 52 (in this example, a woven fiberglass material). The copper channel containing the wires 53 is then wound in a coil having a rectangular cross-section of 6.0 cm×15.25 cm, having 30 layers and 47 turns per layer. The wound coil is then vacuum impregnated with an epoxy compound 54. The finished coils are mounted on an annular stainless steel reverse bobbin 56. A heater blanket 55 is held against the inner face of the bobbin and the windings to protect the assembly in the event of a magnet quench. In an alternate version, the superconducting coil may be formed of 0.8 mm diameter Nb3Sn based strands. These strands can be deployed in a 4 strand cable, heat treated to form the superconducting matrix and soldered into a copper channel of outer dimension 3.19 by 2.57 mm. The integrated cable in channel conductor can be insulated with overlapped woven fiberglass tape and then wound into coils of 49 turns and 26 layers deep with a rectangular cross section of 79.79 mm by 180.5 mm and inner radius of 374.65 mm. The wound coil is then vacuum impregnated with an epoxy compound. The entire coil can then be covered with copper sheets to provide thermal conductivity and mechanical stability and then contained in an additional layer of epoxy. The precompression of the coil can be provided by heating the stainless steel reverse bobbin and fitting the coils within the reverse bobbin. The reverse bobbin inner diameter is chosen so that when the entire mass is cooled to 4 K, the reverse bobbin stays in contact with the coil and provides some compression. Heating the stainless steel reverse bobbin to approximately 50 degrees C. and fitting coils at room temperature (20 degrees C.) can achieve this.

The geometry of the coil is maintained by mounting the coils in a "reverse" rectangular bobbin 56 and incorporating a pre-compression stainless steel bladder 58 between each coil and an inner face 57 of the bobbin to exert a restorative force 60 that works against the distorting force produced when the coils are energized. The bladder is pre-compressed after the coils and the heater blanket are assembled on the bobbin, by injecting epoxy into the bladder and allowing it to harden. The precompression force of the bladder is set to minimize the strain in the brittle Nb3Sn superconducting matrix through all phases of cool-down and magnet energizing.

Figure 5:
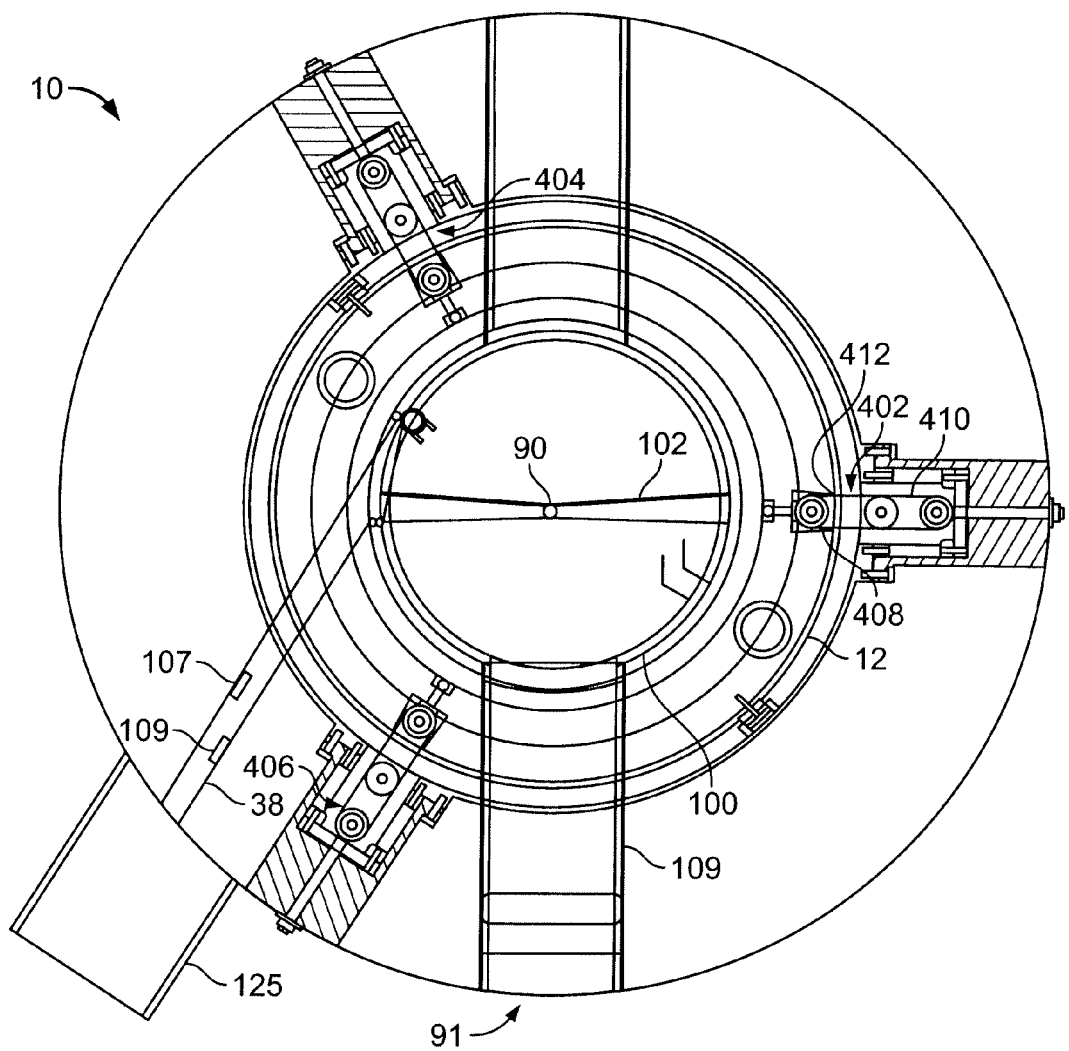
Figure 6:
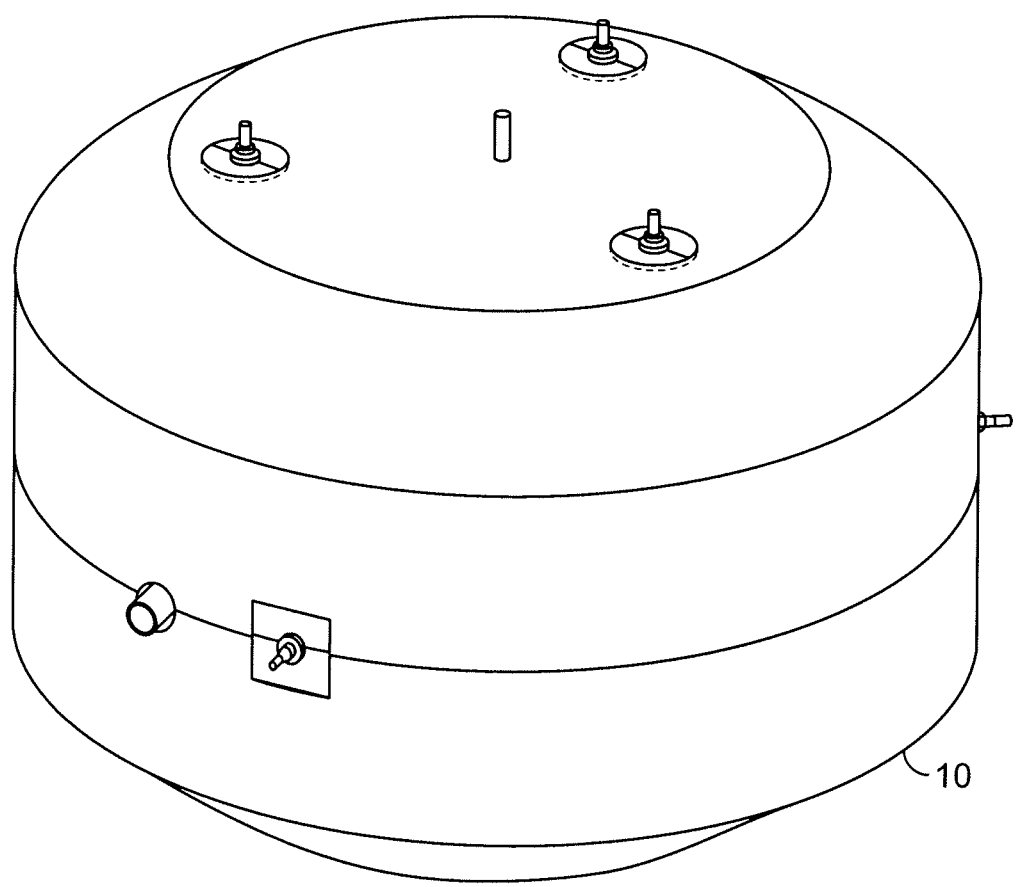
FIG. 6 is a perspective view of a synchrocyclotron.

As shown in FIG. 5, the coil position is maintained relative to the magnet yoke and cryostat using a set of warm-to-cold support straps 402, 404, 406. Supporting the cold mass with thin straps reduces the heat leakage imparted to the cold mass by the rigid support system. The straps are arranged to withstand the varying gravitational force on the coil as the magnet rotates on board the gantry. They withstand the combined effects of gravity and the large de-centering force realized by the coil when it is perturbed from a perfectly symmetric position relative to the magnet yoke. Additionally the links act to reduce dynamic forces imparted on the coil as the gantry accelerates and decelerates when its position is changed. Each warm-to-cold support includes 3 S2 fiberglass links. Two links 410, 412 are supported across pins between the warm yoke and an intermediate temperature (50-70 K), and one link 408 is supported across the intermediate temperature pin and a pin attached to the cold mass. Each link is 10.2 cm long (pin center to pin center) and is 20 mm wide. The link thickness is 1.59 mm. Each pin is made of stainless steel and is 47.7 mm in diameter.

Figure 3:
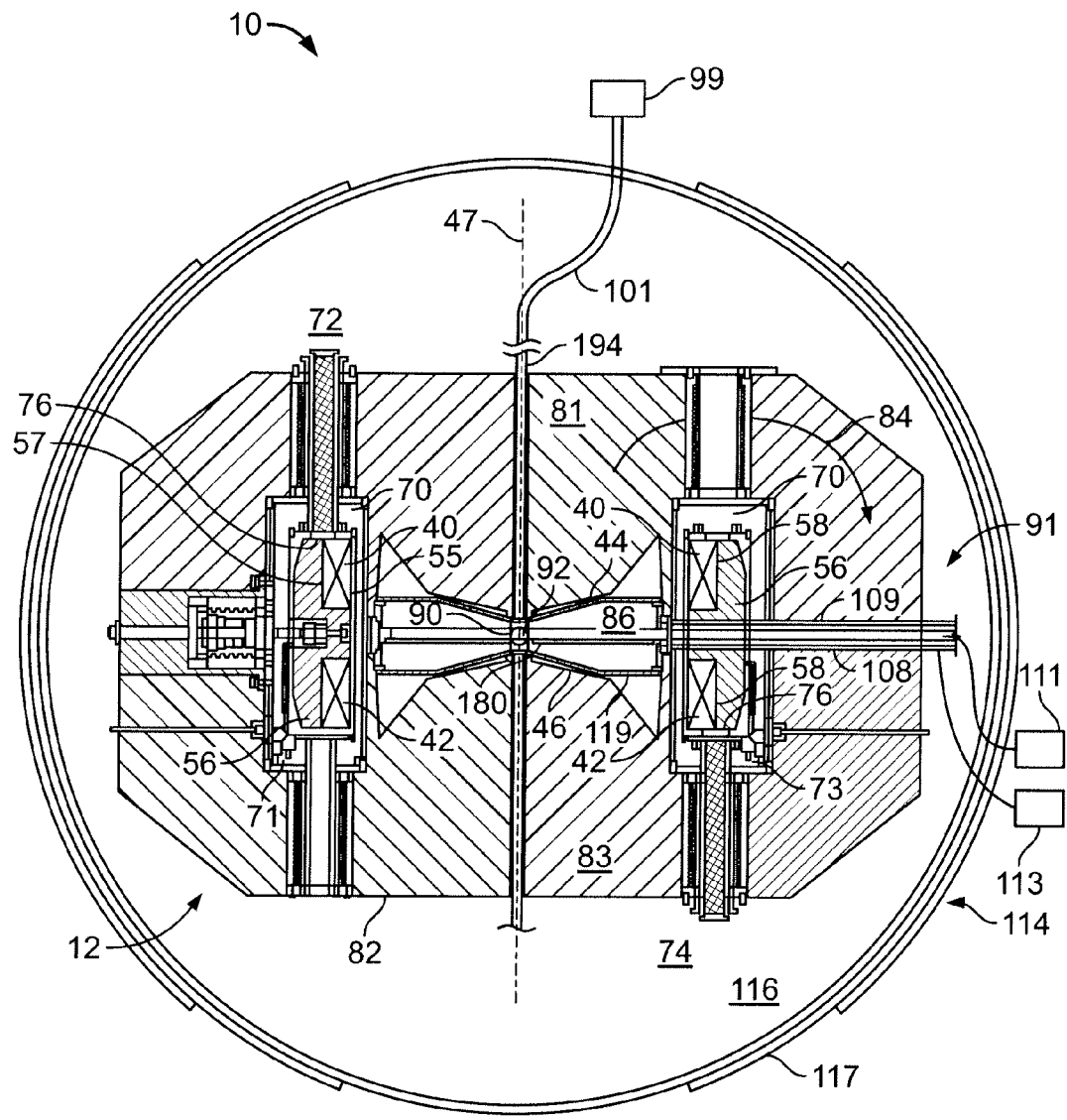
FIGS. 3, 4, and 5 are cross-sectional views of a synchrocyclotron.
Figure 4:
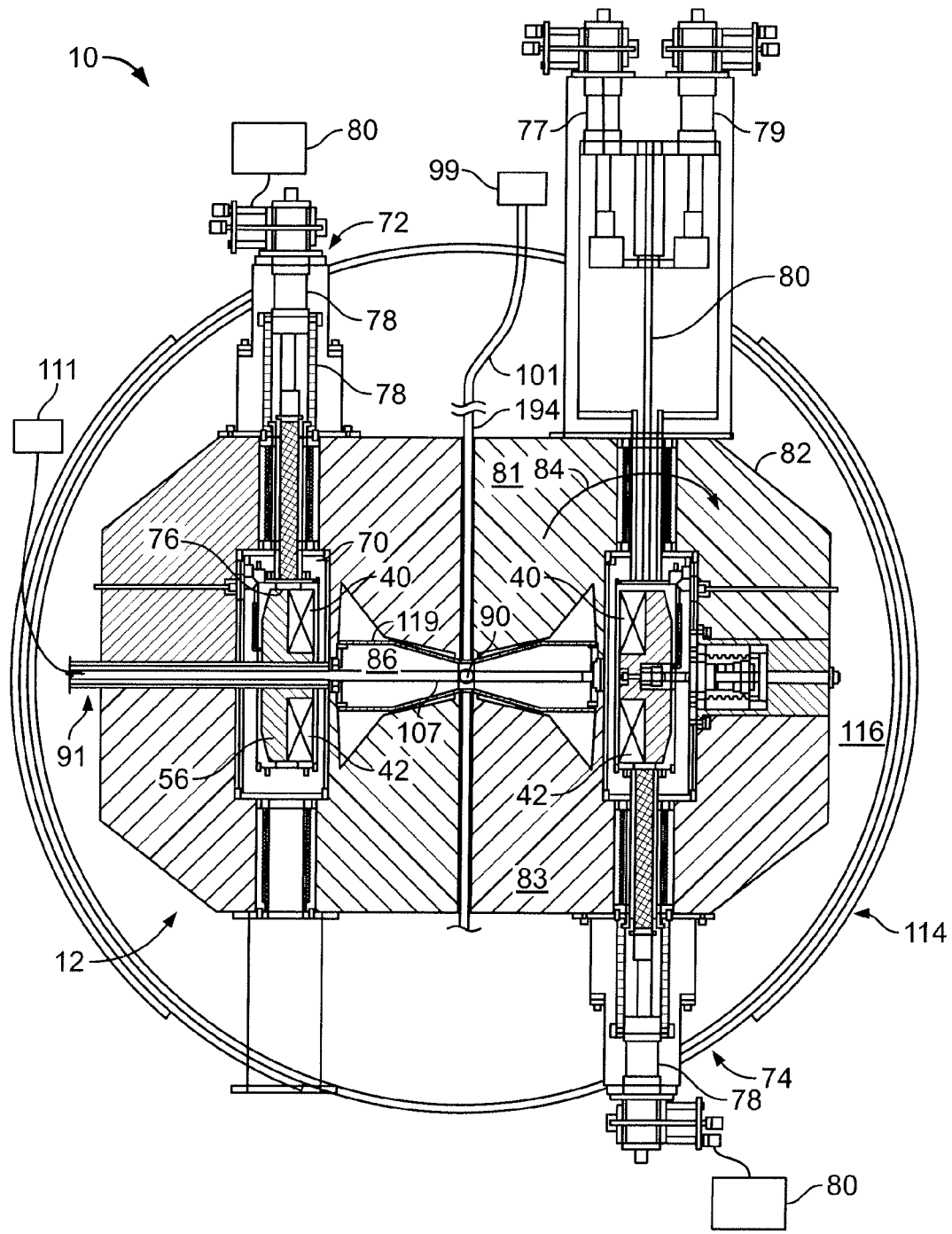

Referring to FIG. 3, the field strength profile as a function of radius is determined largely by choice of coil geometry; the pole faces 44, 46 of the permeable yoke material can be contoured to fine tune the shape of the magnetic field to ensure that the particle beam remains focused during acceleration.

The superconducting coils are maintained at temperatures near absolute zero (e.g., about 4 degrees Kelvin) by enclosing the coil assembly (the coils and the bobbin) inside an evacuated annular aluminum or stainless steel cryostatic chamber 70 that provides a free space around the coil structure, except at a limited set of support points 71, 73. In an alternate version (FIG. 4) the outer wall of the cryostat may be made of low carbon steel to provide an additional return flux path for the magnetic field. The temperature near absolute zero is achieved and maintained using two Gifford-McMahon cryo-coolers 72, 74 that are arranged at different positions on the coil assembly. Each cryo-cooler has a cold end 76 in contact with the coil assembly. The cryo-cooler heads 78 are supplied with compressed Helium from a compressor 80. Two other Gifford-McMahon cryo-coolers 77, 79 are arranged to cool high temperature (e.g., 60-80 degrees Kelvin) leads 81 that supply current to the superconducting windings.

The coil assembly and cryostatic chambers are mounted within and fully enclosed by two halves 81, 83 of a pillbox-shaped magnet yoke 82. In this example, the inner diameter of the coil assembly is about 140 cm. The iron yoke 82 provides a path for the return magnetic field flux 84 and magnetically shields the volume 86 between the pole faces 44, 46 to prevent external magnetic influences from perturbing the shape of the magnetic field within that volume. The yoke also serves to decrease the stray magnetic field in the vicinity of the accelerator.

Figure 9:
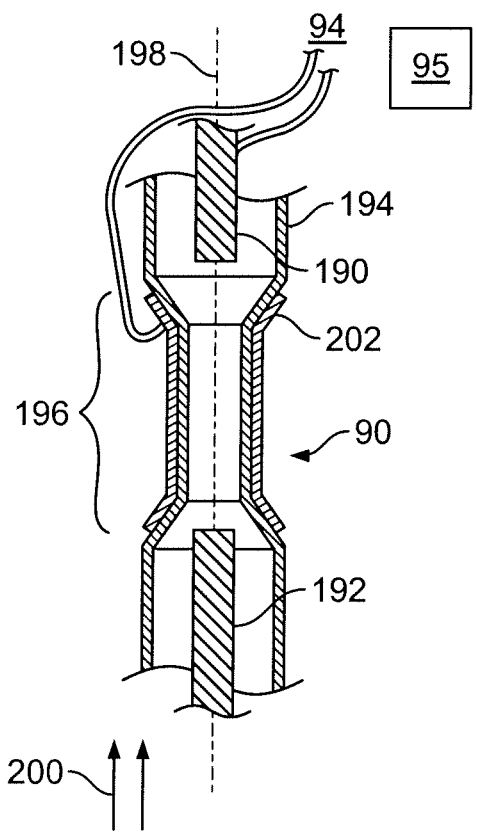
FIG. 9 is a cross-sectional view of an ion source.

As shown in FIGS. 3 and 9, the synchrocyclotron includes an ion source 90 of a Penning ion gauge geometry located near the geometric center 92 of the magnet structure 82. The ion source may be as described below, or the ion source may be of the type described in U.S. patent application Ser. No. 11/948,662, entitled "Interrupted Particle Source", the contents of which are incorporated herein by reference as if set forth in full. Ion source 90 is fed from a supply 99 of hydrogen through a gas line 101 and tube 194 that delivers gaseous hydrogen. Electric cables 94 carry an electric current from a current source 95 to stimulate electron discharge from cathodes 192, 190 that are aligned with the magnetic field, 200.

In this example, the discharged electrons ionize the gas exiting through a small hole from tube 194 to create a supply of positive ions (protons) for acceleration by one semicircular (dee-shaped) radio-frequency plate 100 that spans half of the space enclosed by the magnet structure and one dummy dee plate 102. In the case of an interrupted ion source, all (or a substantial part) of the tube containing plasma is removed at the acceleration region, thereby allowing ions to be more rapidly accelerated in a relatively high magnetic field.

Figure 10:
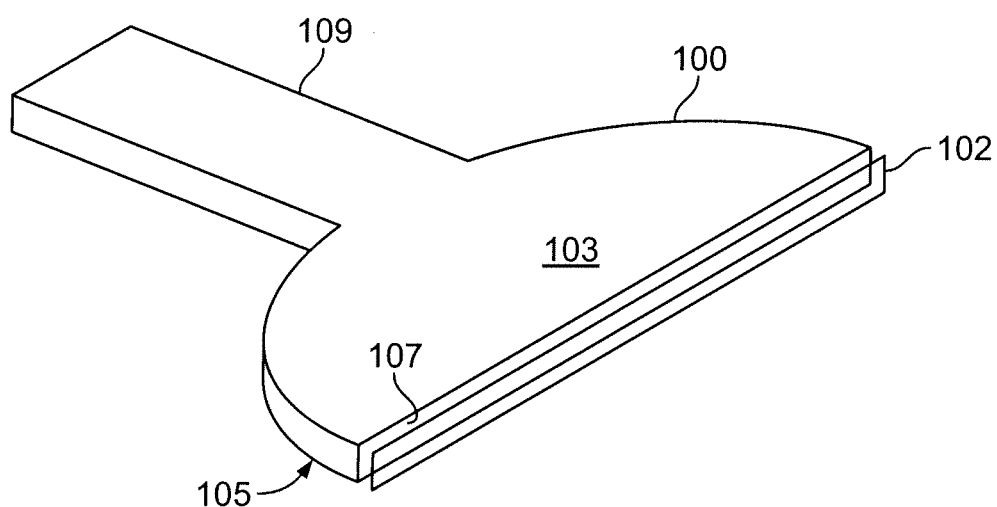
FIG. 10 is a perspective view of a dee plate and a dummy dee.

As shown in FIG. 10, the dee plate 100 is a hollow metal structure that has two semicircular surfaces 103, 105 that enclose a space 107 in which the protons are accelerated during half of their rotation around the space enclosed by the magnet structure. A duct 109 opening into the space 107 extends through the yoke to an external location from which a vacuum pump 111 can be attached to evacuate the space 107 and the rest of the space within a vacuum chamber 119 in which the acceleration takes place. The dummy dee 102 comprises a rectangular metal ring that is spaced near to the exposed rim of the dee plate. The dummy dee is grounded to the vacuum chamber and magnet yoke. The dee plate 100 is driven by a radio-frequency signal that is applied at the end of a radio-frequency transmission line to impart an electric field in the space 107. The radio frequency electric field is made to vary in time as the accelerated particle beam increases in distance from the geometric center. Examples of radio frequency waveform generators that are useful for this purpose are described in U.S. patent application Ser. No. 11/187,633, titled "A Programmable Radio Frequency Waveform Generator for a Synchrocyclotron," filed Jul. 21, 2005, and in U.S. Provisional Application No. 60/590,089, same title, filed on Jul. 21, 2004, both of which are incorporated herein by reference as if set forth in full. The radio frequency electric field may be controlled in the manner described in U.S. patent application Ser. No. 11/948,359, entitled "Matching A Resonant Frequency Of A Resonant Cavity To A Frequency Of An Input Voltage", the contents of which are incorporated herein by reference as if set forth in full.

For the beam emerging from the centrally located ion source to clear the ion source structure as it begins to spiral outward, a large voltage difference is required across the radio frequency plates. 20,000 Volts is applied across the radio frequency plates. In some versions from 8,000 to 20,000 Volts may be applied across the radio frequency plates. To reduce the power required to drive this large voltage, the magnet structure is arranged to reduce the capacitance between the radio frequency plates and ground. This is done by forming holes with sufficient clearance from the radio frequency structures through the outer yoke and the cryostat housing and making sufficient space between the magnet pole faces.

The high voltage alternating potential that drives the dee plate has a frequency that is swept downward during the accelerating cycle to account for the increasing relativistic mass of the protons and the decreasing magnetic field. The dummy dee does not require a hollow semi-cylindrical structure as it is at ground potential along with the vacuum chamber walls. Other plate arrangements could be used such as more than one pair of accelerating electrodes driven with different electrical phases or multiples of the fundamental frequency. The RF structure can be tuned to keep the Q high during the required frequency sweep by using, for example, a rotating capacitor having intermeshing rotating and stationary blades. During each meshing of the blades, the capacitance increases, thus lowering the resonant frequency of the RF structure. The blades can be shaped to create a precise frequency sweep required. A drive motor for the rotating condenser can be phase locked to the RF generator for precise control. One bunch of particles is accelerated during each meshing of the blades of the rotating condenser.

The vacuum chamber 119 in which the acceleration occurs is a generally cylindrical container that is thinner in the center and thicker at the rim. The vacuum chamber encloses the RF plates and the ion source and is evacuated by the vacuum pump 111. Maintaining a high vacuum insures that accelerating ions are not lost to collisions with gas molecules and enables the RF voltage to be kept at a higher level without arcing to ground.

Protons traverse a generally spiral path beginning at the ion source. In half of each loop of the spiral path, the protons gain energy as they pass through the RF electric field in space 107. As the ions gain energy, the radius of the central orbit of each successive loop of their spiral path is larger than the prior loop until the loop radius reaches the maximum radius of the pole face. At that location a magnetic and electric field perturbation directs ions into an area where the magnetic field rapidly decreases, and the ions depart the area of the high magnetic field and are directed through an evacuated tube 38 to exit the yoke of the cyclotron. The ions exiting the cyclotron will tend to disperse as they enter the area of markedly decreased magnetic field that exists in the room around the cyclotron. Beam shaping elements 107, 109 in the extraction channel 38 redirect the ions so that they stay in a straight beam of limited spatial extent.

The magnetic field within the pole gap needs to have certain properties to maintain the beam within the evacuated chamber as it accelerates. The magnetic field index n, which is shown below, $$n=-(r/B)dB/dr,$$

should be kept positive to maintain this "weak" focusing. Here r is the radius of the beam and B is the magnetic field.

Additionally the field index needs to be maintained below 0.2, because at this value the periodicity of radial oscillations and vertical oscillations of the beam coincide in a $v_r=2 v_z$ resonance. The betatron frequencies are defined by $v_r=(1-n)^{1/2}$ and $v_z=n^{1/2}$. The ferromagnetic pole face is designed to shape the magnetic field generated by the coils so that the field index n is maintained positive and less than 0.2 in the smallest diameter consistent with a 250 MeV beam in the given magnetic field.

As the beam exits the extraction channel it is passed through a beam formation system 125 (FIG. 5) that can be programmably controlled to create a desired combination of scattering angle and range modulation for the beam. Examples of beam forming systems useful for that purpose are described in U.S. patent application Ser. No. 10/949,734, titled "A Programmable Particle Scatterer for Radiation Therapy Beam Formation", filed Sep. 24, 2004, and U.S. Provisional Application No. 60/590,088, filed Jul. 21, 2005, both of which are incorporated herein by reference as if set forth in full. Beam formation system 125 may be used in conjunction with an inner gantry 601, which is described below, to direct a beam to the patient.

During operation, the plates absorb energy from the applied radio frequency field as a result of conductive resistance along the surfaces of the plates. This energy appears as heat and is removed from the plates using water cooling lines 108 that release the heat in a heat exchanger 113 (FIG. 3).

Stray magnetic fields exiting from the cyclotron are limited by both the pillbox magnet yoke (which also serves as a shield) and a separate magnetic shield 114. The separate magnetic shield includes of a layer 117 of ferromagnetic material (e.g., steel or iron) that encloses the pillbox yoke, separated by a space 116. This configuration that includes a sandwich of a yoke, a space, and a shield achieves adequate shielding for a given leakage magnetic field at lower weight.

As mentioned, the gantry allows the synchrocyclotron to be rotated about the horizontal rotational axis 532. The truss structure 516 has two generally parallel spans 580, 582. The synchrocyclotron is cradled between the spans about midway between the legs. The gantry is balanced for rotation about the bearings using counterweights 122, 124 mounted on ends of the legs opposite the truss.

The gantry is driven to rotate by an electric motor mounted to one of the gantry legs and connected to the bearing housings by drive gears and belts or chains. The rotational position of the gantry is derived from signals provided by shaft angle encoders incorporated into the gantry drive motors and the drive gears.

At the location at which the ion beam exits the cyclotron, the beam formation system 125 acts on the ion beam to give it properties suitable for patient treatment. For example, the beam may be spread and its depth of penetration varied to provide uniform radiation across a given target volume. The beam formation system can include passive scattering elements as well as active scanning elements.

All of the active systems of the synchrocyclotron (the current driven superconducting coils, the RF-driven plates, the vacuum pumps for the vacuum acceleration chamber and for the superconducting coil cooling chamber, the current driven ion source, the hydrogen gas source, and the RF plate coolers, for example), are controlled by appropriate synchrocyclotron control electronics (not shown), which may include, e.g., a computer programmed with appropriate programs to effect control.

The control of the gantry, the patient support, the active beam shaping elements, and the synchrocyclotron to perform a therapy session is achieved by appropriate therapy control electronics (not shown).

Figure 11:
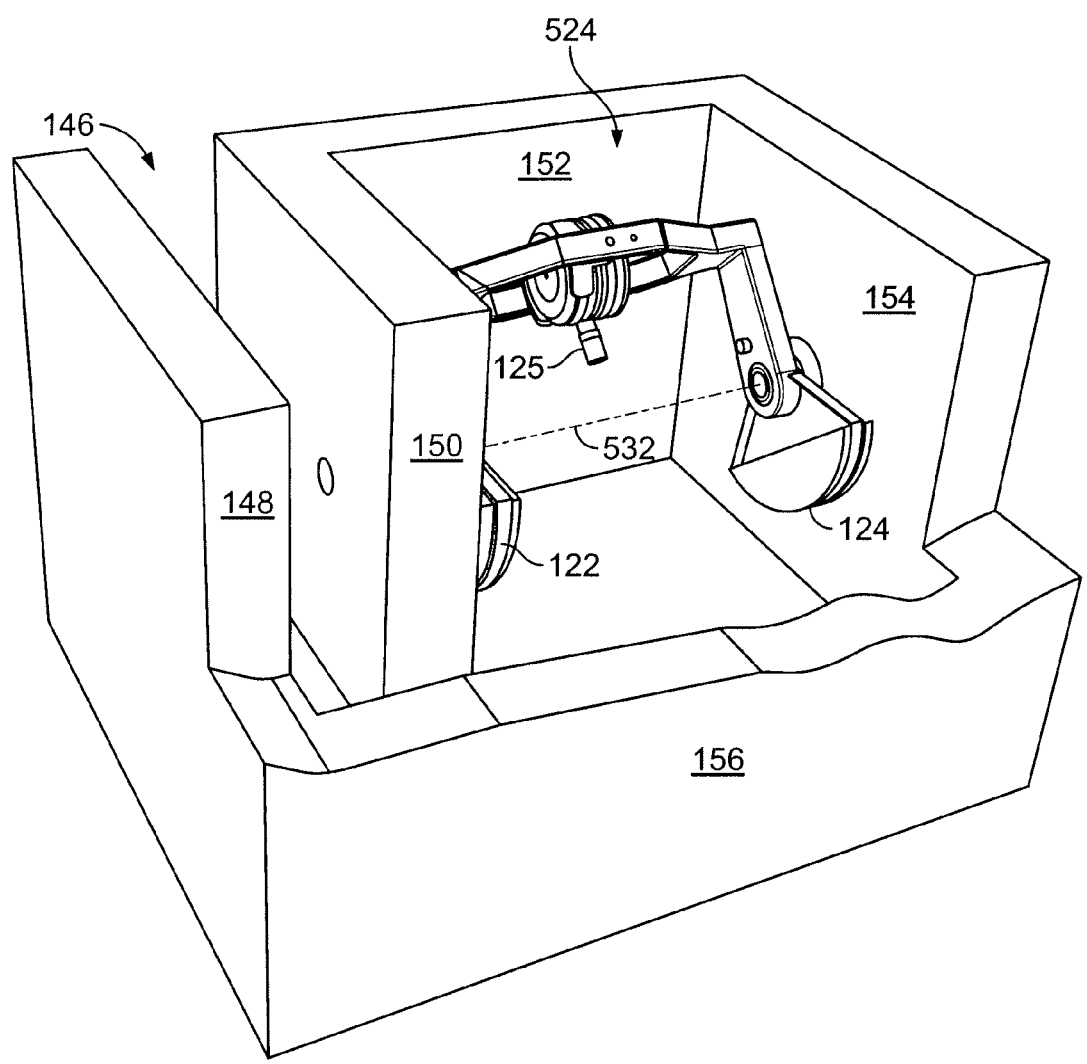
FIG. 11 is a perspective view of a vault.
Figure 12:
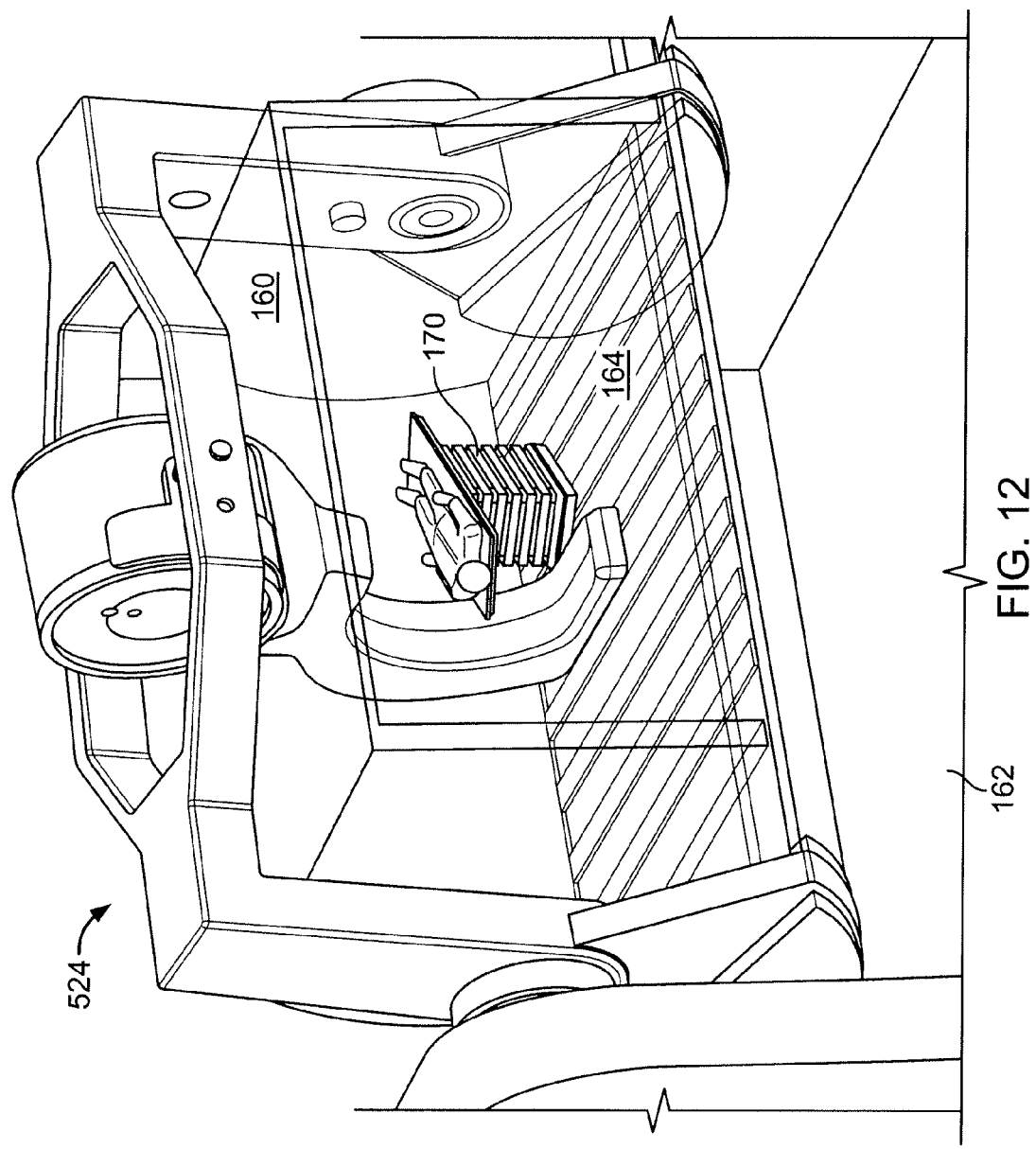
FIG. 12 is a perspective view of a treatment room with a vault.

As shown in FIGS. 1, 11, and 12, the gantry bearings are supported by the walls of a cyclotron vault 524. The gantry enables the cyclotron to be swung through a range 520 of 180 degrees (or more) including positions above, to the side of, and below the patient. The vault is tall enough to clear the gantry at the top and bottom extremes of its motion. A maze 146 sided by walls 148, 150 provides an entry and exit route for therapists and patients. Because at least one wall 152 is never in line with the proton beam directly from the cyclotron, it can be made relatively thin and still perform its shielding function. The other three side walls 154, 156, 150/148 of the room, which may need to be more heavily shielded, can be buried within an earthen hill (not shown). The required thickness of walls 154, 156, and 158 can be reduced, because the earth can itself provide some of the needed shielding.

Figure 13:
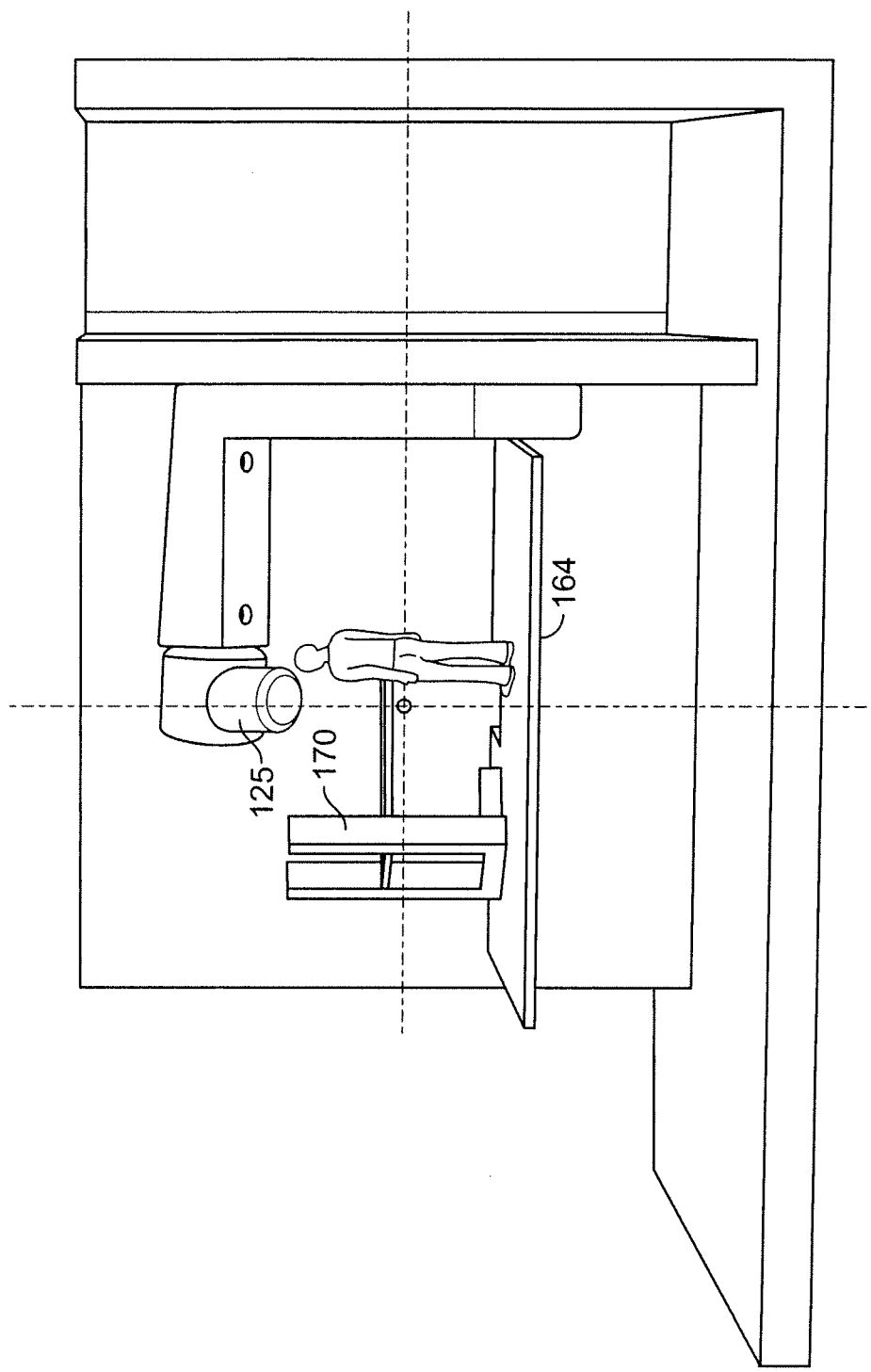
FIG. 13 shows a profile of one-half of a symmetrical profile of a pole face and a pole piece.

Referring to FIGS. 12 and 13, for safety and aesthetic reasons, a therapy room 160 may be constructed within the vault. The therapy room is cantilevered from walls 154, 156, 150 and the base 162 of the containing room into the space between the gantry legs in a manner that clears the swinging gantry and also maximizes the extent of the floor space 164 of the therapy room. Periodic servicing of the accelerator can be accomplished in the space below the raised floor. When the accelerator is rotated to the down position on the gantry, full access to the accelerator is possible in a space separate from the treatment area. Power supplies, cooling equipment, vacuum pumps and other support equipment can be located under the raised floor in this separate space.

Within the treatment room, the patient support 170 can be mounted in a variety of ways that permit the support to be raised and lowered and the patient to be rotated and moved to a variety of positions and orientations.

Figure 14:
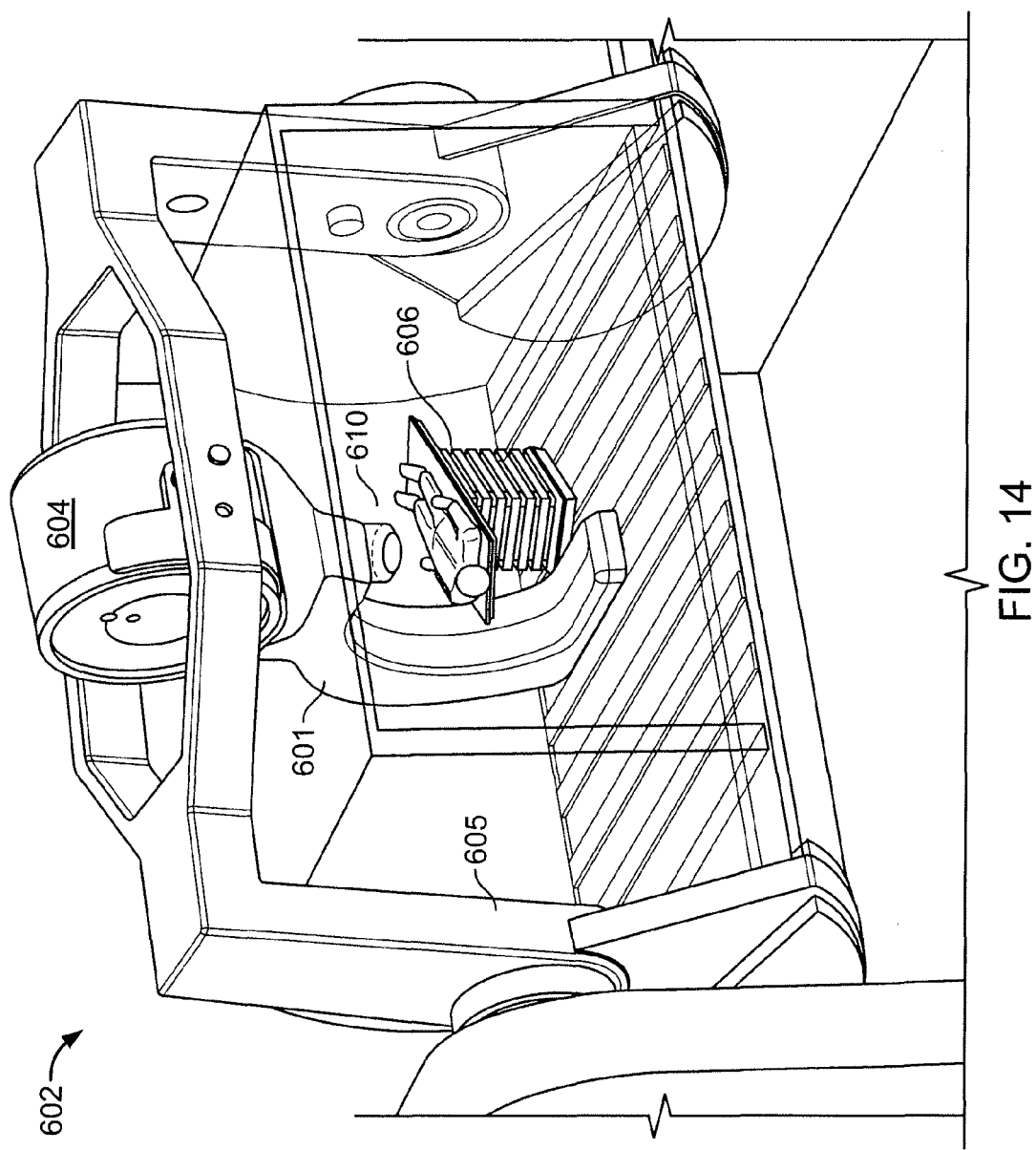
FIG. 14 shows a patient positioned within an inner gantry in a treatment room.

In system 602 of FIG. 14, a beam-producing particle accelerator, in this case synchrocyclotron 604, is mounted on rotating gantry 605. Rotating gantry 605 is of the type described herein, and can angularly rotate around patient support 606. This feature enables synchrocyclotron 604 to provide a particle beam directly to the patient from various angles. For example, as in FIG. 14, if synchrocyclotron 604 is above patient support 606, the particle beam may be directed downwards toward the patient. Alternatively, if synchrocyclotron 604 is below patient support 606, the particle beam may be directed upwards toward the patient. The particle beam is applied directly to the patient in the sense that an intermediary beam routing mechanism is not required. A routing mechanism, in this context, is different from a shaping or sizing mechanism in that a shaping or sizing mechanism does not re-route the beam, but rather sizes and/or shapes the beam while maintaining the same general trajectory of the beam.

Figure 15:
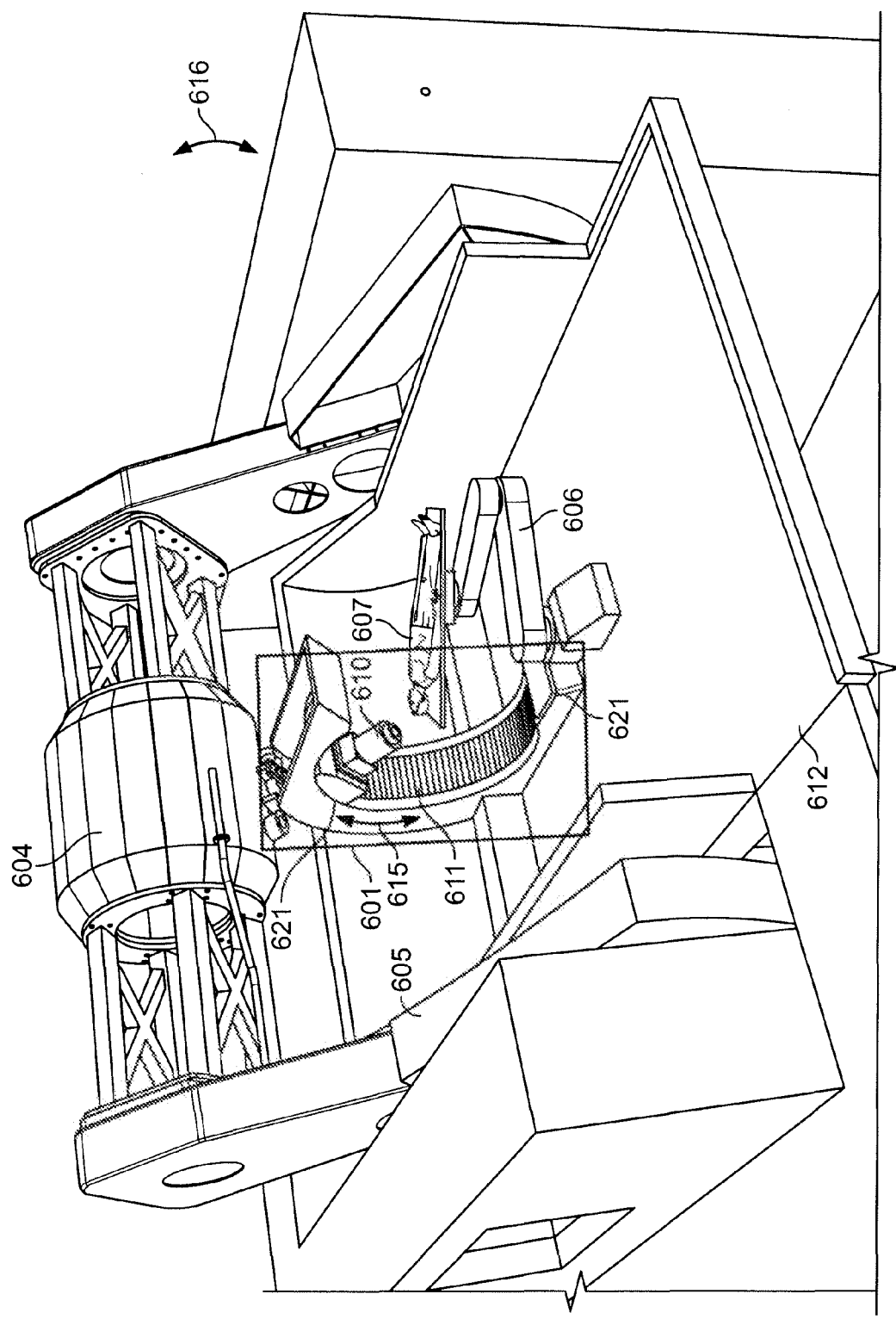
FIG. 15 is a perspective view showing both the outer and inner gantries positioned to apply a proton or ion beam from above the patient.
Figure 16:
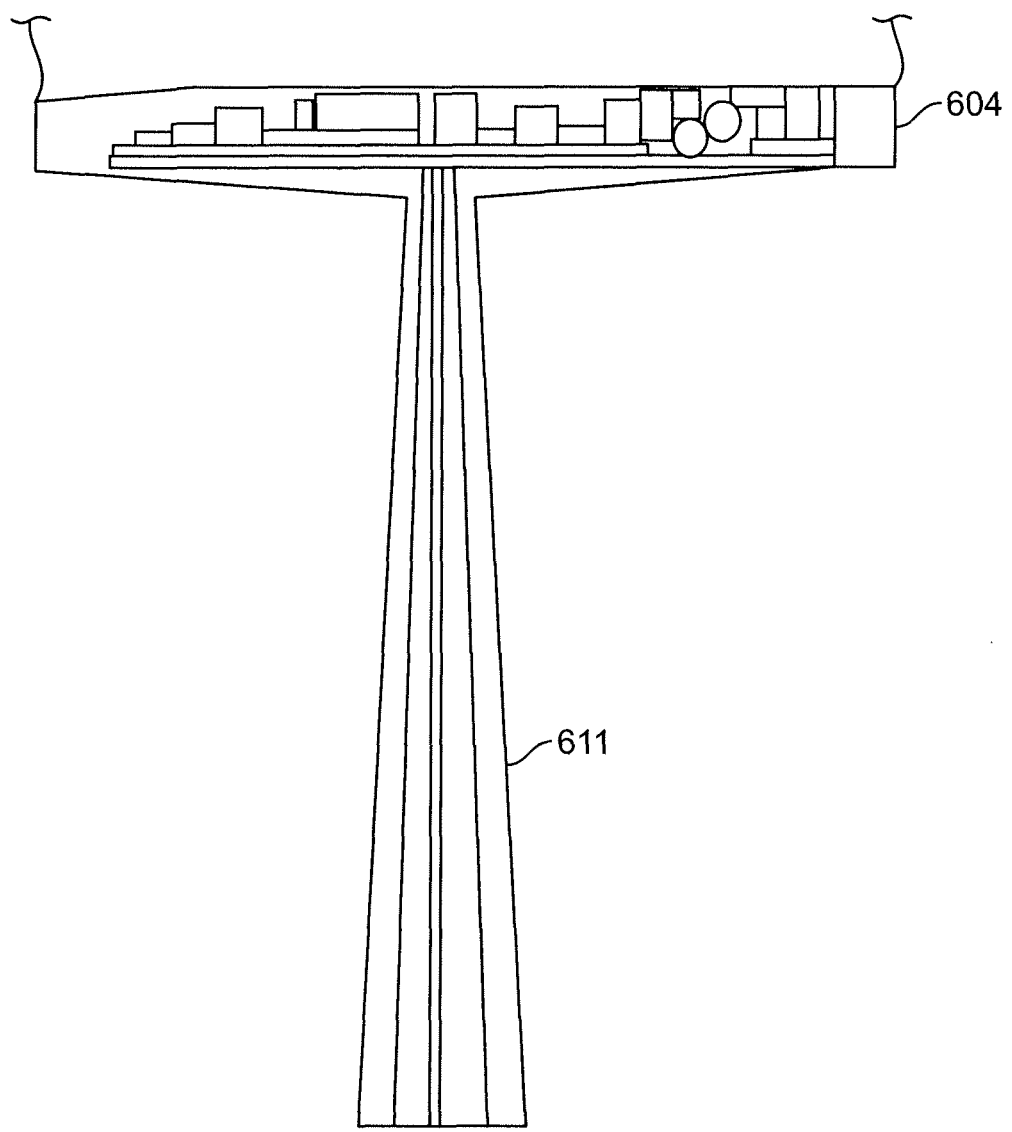
FIG. 16 shows the shape of a particle beam provided by an accelerator.

Referring also to FIG. 15, an inner gantry 601 may be included system 602. In this example, inner gantry 601 is roughly C-shaped, as shown. Inner gantry 601 includes an applicator 610. Applicator 610 is mounted in a manner that permits applicator 610 to move along the surface 611 of inner gantry 601 relative to patient support 606 (which is a different type of support than that depicted in FIG. 12). This enables the applicator to be positioned anywhere within, e.g., a half-circle around the patient, e.g., anywhere above, alongside, or below the patient 607. Applicator 610 may alter the particle beam provided by synchrocyclotron 604. More specifically, as shown in FIG. 16, the particle beam 611 provided by the beam shaping system of synchrocyclotron 604 may diverge the further the particle beam gets from the output of synchrocyclotron 604. Applicator 610 may receive the particle beam from the output of synchrocyclotron 604 and alter characteristics of the particle beam. For example, applicator 610 may include an aperture and/or other beam-focusing mechanisms to substantially collimate the particle beam. As a result, the particle beam can be more precisely applied to a target in the patient. For example, the particle beam can be sized and/or shaped to treat tumors of specific sizes and/or shapes. In this regard, applicator 610 is not limited to collimating the particle beam. For example, applicator 610 may reduce the size of the particle beam while also collimating the beam. The applicator may be a multi-leaf collimator for sizing and/or shaping the particle beam. Applicator 610 may also simply allow the particle beam to pass without alteration. Applicator 610 may be computer controlled to affect the size and/or shape of the beam, as desired.

Figure 17:
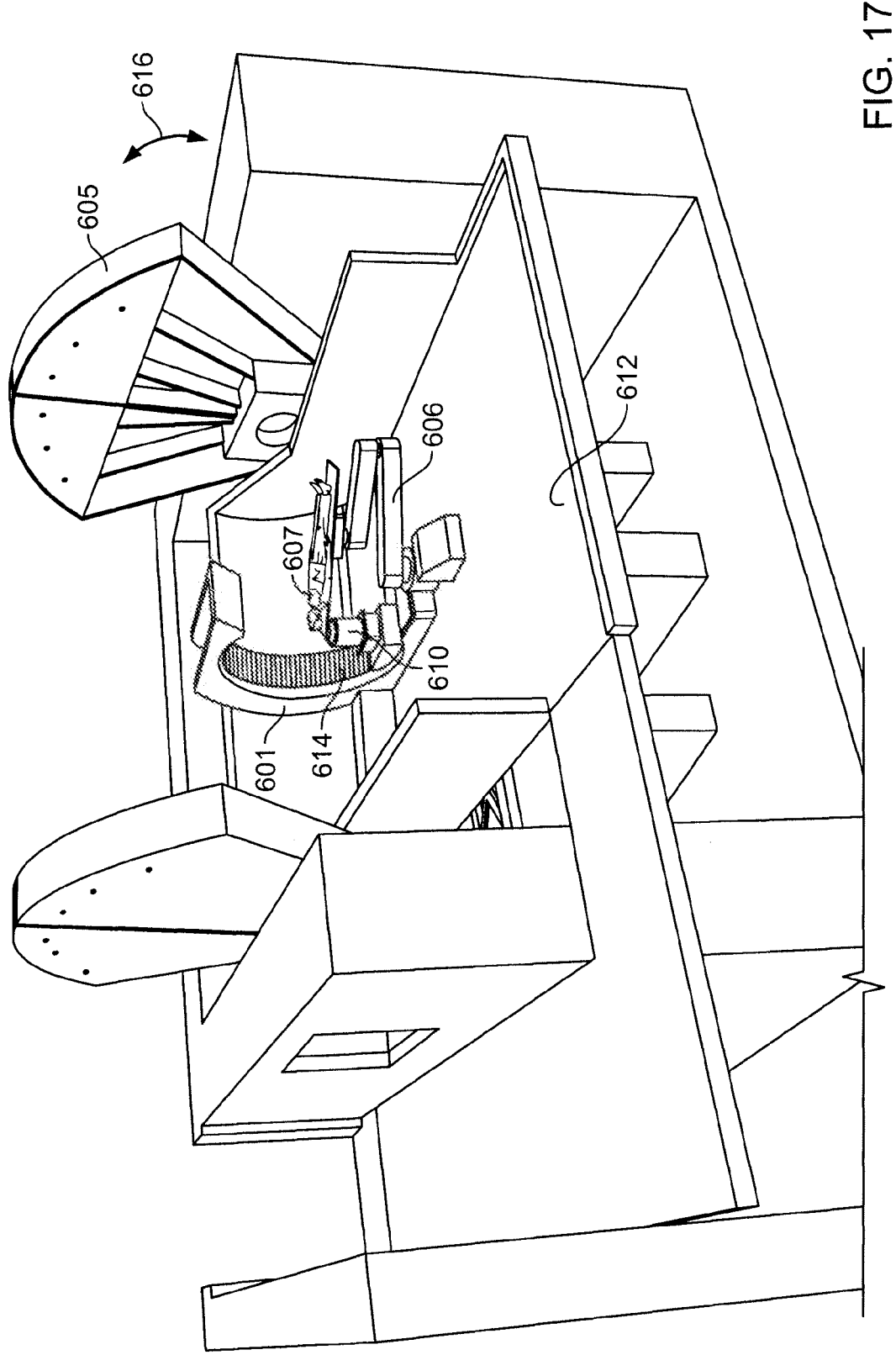
FIG. 17 is a perspective view showing both the outer and inner gantries positioned to apply a proton or ion beam from above below the patient.

Applicator 610 and synchrocyclotron 604 may move relative to patient support 606 (and thus the patient) and relative to one another. For example, movement of applicator 610 may substantially coincide with rotation of gantry 605, or one may follow the other, so that the output of synchrocyclotron 604 aligns to the input of applicator 610. FIGS. 15 and 17 illustrate movement of gantry 605 and movement of applicator 610 along inner gantry 601. More specifically, FIG. 17 shows a case where gantry 605 is rotated such that synchrocyclotron 604 is in a vault below patient support 606. In FIG. 17, synchrocyclotron 604 is below the floor 612 of the treatment room, which floor may be made of concrete. Therefore, synchrocyclotron 604 is not visible in FIG. 17. In this case, applicator 610 is moved along inner gantry 601 so that applicator 610 aligns to the output of synchrocyclotron 604. Because synchrocyclotron 604 is not shown in FIG. 17, this alignment is not visible. Nevertheless, a particle beam output from synchrocyclotron 604 passes through cover 614 of inner gantry 601 and a corresponding hole in the floor (not shown) and is thereafter is received by applicator 610. Applicator 610 performs any alteration on the particle beam, and passes the particle beam to patient 607.

Gantry 605 (and thus synchrocyclotron 604) is rotatable relative to the patient in the directions of arrow 615. Applicator 610 is movable along inner gantry 601 in the directions of arrow 616. FIG. 15 shows the locations of synchrocyclotron 604 and applicator 610 after the movements depicted by arrows 615 and 616, respectively. In FIG. 15, both synchrocyclotron 604 and applicator 610 are above patient support 606 (and thus above patient 607). In this configuration, synchrocyclotron 604 directs its particle beam downward, toward the patient. Applicator 610 receives the particle beam, alters (e.g., collimates) the particle beam, and passes the resulting particle beam to the patient.

Patient support 606 is movable relative to inner gantry 601, thereby enabling the patient to be moved such that a top part 621 of inner gantry 601 is above the patient, and such that a bottom part 622 of inner gantry 601 is below the patient. Movement of patient support 606, along with movement of gantry 605 and applicator 610, enables relatively precise targeting of tumors and/or other treatment areas on the patient.

Figure 18:
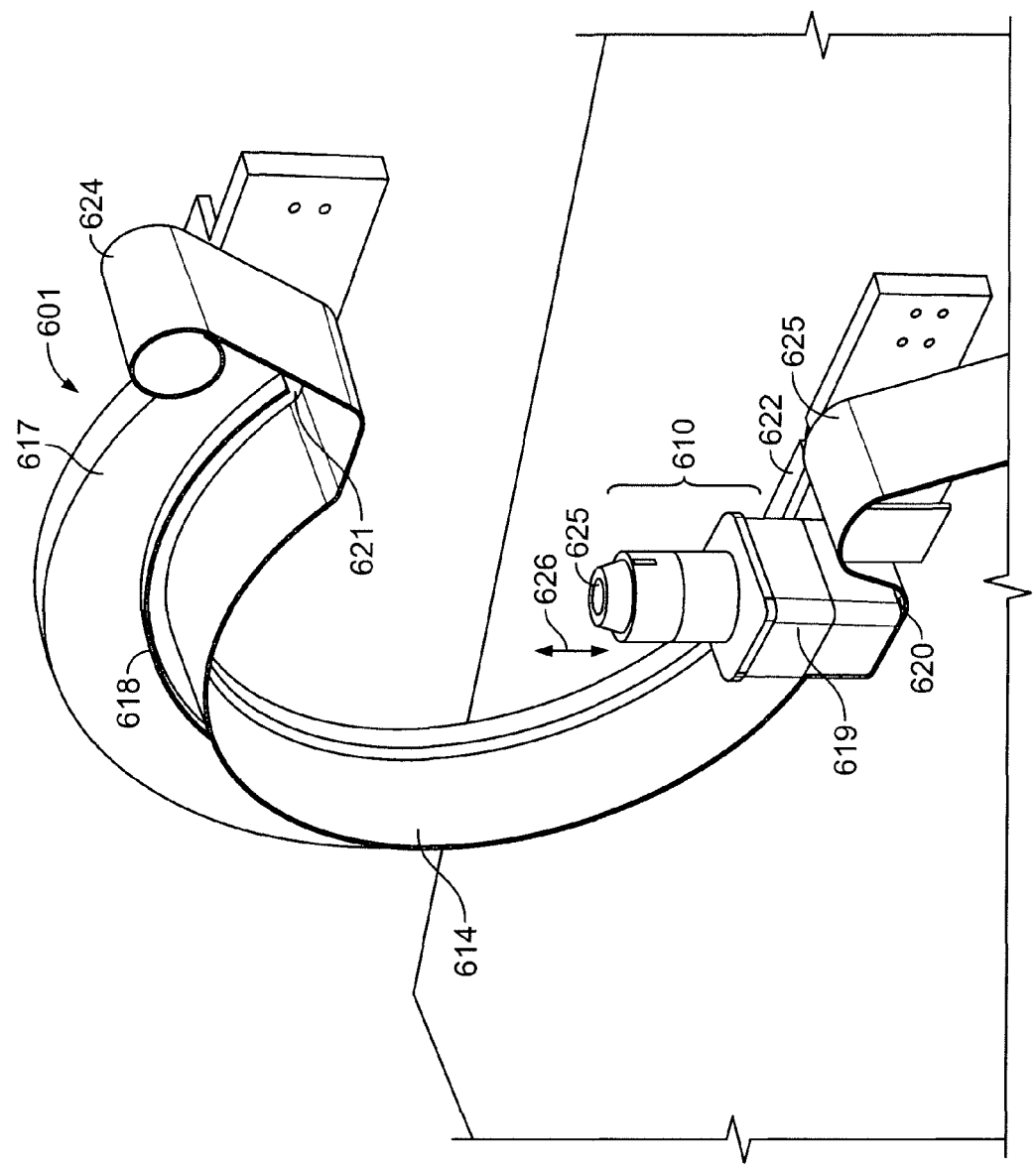
FIG. 18 shows components of the inner gantry.

FIG. 18 shows an example construction of inner gantry 601. In this example, inner gantry includes a structural weldment 617, a precision linear bearing rail 618 (e.g., a THK rail), cover 614, and applicator 610 that includes an extension drive 619, and a theta drive 620. Inner gantry 601 may include features in addition to those show, substitutions for the features that are shown, or both.

Structural weldment 617 may be constructed of any rigid material, such as metal, plastic, or the like, which is capable of supporting the weight of applicator 610. In this example, structural weldment 617 is substantially C-shaped (thereby defining the shape of inner gantry 601). It is noted, however, that structural weldment 617 may have other shapes. For example, it may be elongated or compressed. Basically, structural weldment may have any shape that enables relatively unobstructed, continuous travel of applicator 610 between positions that are above and below the patient.

Structural weldment 617 includes one or more bearing rails 618. The number of rails that may be used depends upon the connection required to applicator 610. Applicator 610 moves along bearing rail 618 between a top part 621 of structural weldment 617 and a bottom part 622 of structural weldment 617. The movement may be continuous or in discrete increments and may be stopped at any point along bearing rail 618 in order to obtain a desired position of applicator 610 relative to the position of the patient.

Cover 614 covers what would otherwise be an open hole to the area below floor 612 (see FIG. 17). The hole and cover allow a particle beam to pass from the synchrocyclotron to the applicator. Cover 614, however, prevents objects and/or other material from falling through that hole and possibly damaging sensitive equipment, such as the synchrocyclotron. Cover 614 may assist in, or control, movement of applicator 610 along bearing rail 618. That is, cover 614 may roll along a path between the top part 621 and the bottom part 622 of structural weldment 617. Cover 614 may roll-up at its ends 624 and/or 625, as shown in FIG. 18.

Applicator 610 includes extension drive 619 and theta drive 620. Extension drive 619 moves aperture 625 towards, and away from, the patent, e.g., along arrow 626. By virtue of this movement, extension drive may modify the projection of the aperture 625 on the patient. For example, the size of the aperture may be increased or decreased. The shape of the aperture may be altered as well, e.g., between a circular shape, an oval shape, a polygonal shape, etc. Theta drive 620 moves applicator 610 along rail 618 between top part 621 and bottom part 622 of structural weldment 617. Cover 614 may travel along with applicator 610.

All or part of extension drive 619 and theta drive 620 may be computer-controlled. For example, extension drive 619 and/or theta drive 620 may be controlled by the same hardware and/or software that is used to control gantry 605.

Figure 19:
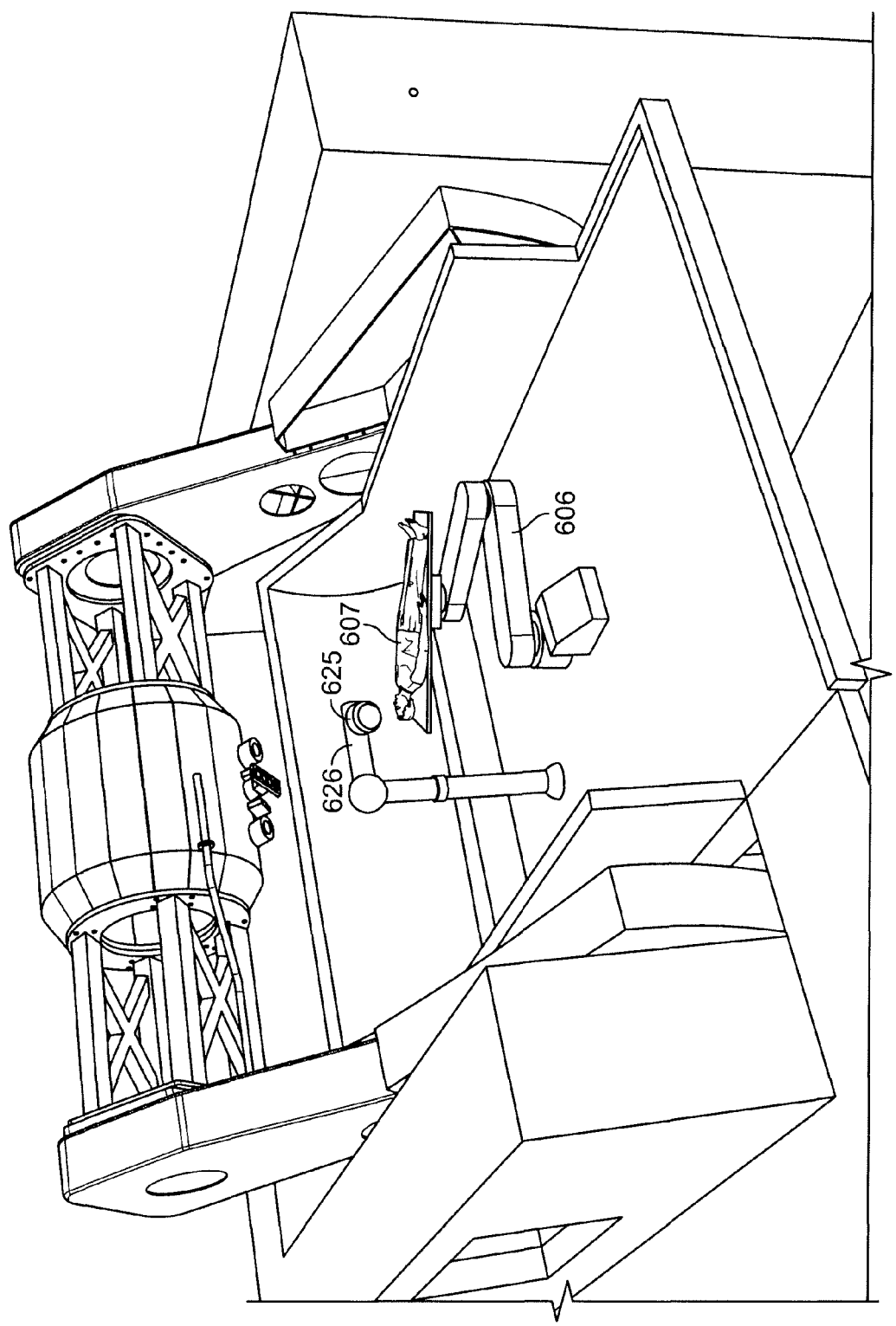
FIG. 19 shows a robotic arm used to perform functions of the inner gantry.

System 602 is not limited to use with inner gantry 601. Any other mechanism may be used to provide an aperture to size and/or shape (e.g., collimate) a particle beam provided by synchrocyclotron 604. For example, referring to FIG. 19, a robotic arm 626 may be used to position an aperture 625 between synchrocyclotron 604 and the patient. The robotic arm may move the aperture in three dimensions (e.g., XYZ Cartesian coordinates) relative to the patent. The robotic arm may be controlled by the same hardware and/or software that is used to control gantry 605. Additionally, the aperture itself may be controlled so that its size and/or shape is modified. As described above, the size of the aperture may be increased or decreased. The shape of the aperture may be altered as well, e.g., between a circular shape, an oval shape, a polygonal shape, etc.

An aperture, such as those described above, may be positioned and/or controlled manually. For example, a stand (not shown) may be used to hold the aperture. The aperture may be sized and/or shaped and placed on the stand. Both the stand and the aperture may be positioned relative to the patent and in line with the particle beam provided by the synchrocyclotron. Any mechanism to hold the aperture may be used. In some implementations, the aperture and/or device used to hold the aperture may be mounted to the synchrocyclotron itself.

The inner gantry is advantageous in that it reduces the precision with which the outer gantry must rotate. For example, the inner gantry allows sub-millimeter beam positioning. Because of the additional precision added by the inner gantry, the outer gantry need not provide sub-millimeter precision, but rather its precision may be at, or greater than, a millimeter. The outer gantry also need not be as large as would otherwise be required in order to obtain high levels of precision.

Additional information concerning the design of the particle accelerator described herein can be found in U.S. Provisional Application No. 60/760,788, entitled "High-Field Superconducting Synchrocyclotron" and filed Jan. 20, 2006; U.S. patent application Ser. No. 11/463,402, entitled "Magnet Structure For Particle Acceleration" and filed Aug. 9, 2006; and U.S. Provisional Application No. 60/850,565, entitled "Cryogenic Vacuum Break Pneumatic Thermal Coupler" and filed Oct. 10, 2006, all of which are incorporated herein by reference as if set forth in full.

Other implementations are within the scope of the following claims. Elements of different implementations, including features incorporated herein by reference, may be combined to form implementations not specifically described herein.

What is claimed is:

1. A system comprising:
   a patient support to hold a patient;
   a particle accelerator to produce a proton or ion beam having an energy level sufficient to reach a target in the patient;
   a gantry on which the particle accelerator is mounted to move the particle accelerator through a range of positions around the patient on the patient support;
   scanning elements that act on the proton or ion beam, the scanning elements being between the patient and a location at which the proton or ion beam exits the particle accelerator; and
   an aperture between the particle accelerator and the patient, the aperture being configurable to alter the proton or ion beam prior to the proton or ion beam reaching the target, the aperture being movable in multiple dimensions relative to the patient.

2. The system of claim 1, wherein the particle accelerator comprises a magnetic structure that defines a cavity to accelerate particles to produce the proton or ion beam; and
   wherein the magnetic structure defines an extraction channel to receive the particles, the extraction channel comprising beam shaping elements to direct the particles and to output the proton or ion beam from the particle accelerator.

3. The system of claim 2, wherein the magnetic structure comprises two halves, each of the halves being associated with a respective superconducting coil for carrying current to generate a magnetic field in the cavity to cause the particles in the cavity to travel in a spiral path that increases in radius as the particles move around the cavity prior to output to the extraction channel.

4. The system of claim 3, wherein each of the halves comprises a pole face configured to shape the magnetic field so that a field index is kept positive to maintain weak focusing within the cavity.

5. The system of claim 1, wherein the particle accelerator comprises superconducting coils for carrying current to generate a magnetic field in a cavity to cause particles to travel in a spiral path; and
   wherein the particle accelerator comprises a helium-based cooling system to cool the superconducting coils to a superconducting temperature.

6. The system of claim 1, wherein the particle accelerator comprises:
   superconducting coils to generate a magnetic field to support production of the proton or ion beam;
   a cold mass holding the superconducting coils; and
   straps to support the cold mass during movement of the gantry.

7. The system of claim 6, wherein the particle accelerator comprises:
   a support structure that houses the cold mass; and
   straps to support the cold mass within the support structure during movement of the gantry, each of the straps comprising two links, a first of the two links connecting to the support structure, and a second of the two links connecting to the cold mass.

8. The system of claim 7, wherein the two links comprise a fiberglass link.

9. The system of claim 1, wherein the particle accelerator is a superconducting synchrocyclotron.

10. The system of claim 9, wherein the superconducting synchrocyclotron is configured to produce a maximum magnetic field between 6 Tesla (T) and 20T, and wherein the energy level is between 150 MeV and 300 MeV.

11. The system of claim 1, wherein the aperture is configurable to alter a size of the proton or ion beam.

12. The system of claim 1, wherein the aperture is configurable to alter a shape of the proton or ion beam.

13. The system of claim 1, wherein the aperture comprises a collimator having multiple leaves.

14. A system comprising:
   a particle accelerator to produce a particle beam having an energy level of at least 150 MeV to reach a target in a patient;
   a gantry on which the particle accelerator is mounted to move the particle accelerator through a range of positions around the patient in order to direct the particle beam towards the target in the patient absent a beam routing mechanism;
   scanning elements that act on the particle beam, the scanning elements system being between the patient and a location at which the particle beam exits the particle accelerator;
   a collimator comprising multiple leaves configured to size the particle beam, to shape the particle beam, or both to size the particle beam and to shape the particle beam prior to the particle beam reaching the target; and
   a computer system to control operation of the collimator.

15. The system of claim 14, wherein the gantry is an outer gantry and wherein the system further comprises:
   an inner gantry on which the collimator is mounted to move the collimator relative to the patent and relative to the particle accelerator.

16. The system of claim 14, wherein the collimator is configured for movement in at least two dimensions relative to the patient.

17. The system of claim 14, wherein the collimator is configured for movement in three dimensions relative to the patient.

18. The system of claim 14, wherein the particle accelerator comprises a magnetic structure that defines a cavity to accelerate particles to produce the proton or ion beam; and
wherein the magnetic structure defines an extraction channel to receive the particles, the extraction channel comprising beam shaping elements to direct the particles and to output the proton or ion beam from the particle accelerator.

19. The system of claim 18, wherein the magnetic structure comprises two halves, each of the halves being associated with a respective superconducting coil for carrying current to generate a magnetic field in the cavity to cause the particles in the cavity to travel in a spiral path that increases in radius as the particles move around the cavity prior to output to the extraction channel.

20. The system of claim 19, wherein each of the halves comprises a pole face configured to shape the magnetic field so that a field index is kept positive to maintain weak focusing within the cavity.

21. The system of claim 18, wherein the particle accelerator comprises superconducting coils within the magnetic structure for carrying current to generate a magnetic field in the cavity to cause the particles to travel in a spiral path; and
wherein the particle accelerator comprises a helium-based cooling system to cool the superconducting coils to a superconducting temperature.

22. The system of claim 14, wherein the particle accelerator comprises:
superconducting coils to generate a magnetic field to support production of the proton or ion beam;
a cold mass holding the superconducting coils; and
straps to support the cold mass during movement of the gantry.

23. The system of claim 22, wherein the particle accelerator comprises:
a support structure that houses the cold mass; and
straps to support the cold mass within the support structure during movement of the gantry, each of the straps comprising two links, a first of the two links connecting to the support structure, and a second of the two links connecting to the cold mass.

* * * * *